US008513241B2

(12) United States Patent
Cervi et al.

(10) Patent No.: US 8,513,241 B2
(45) Date of Patent: Aug. 20, 2013

(54) 3,4-DIHYDRO-2H-PYRAZINO[1,2-A]INDOL-1-ONE DERIVATIVES ACTIVE AS KINASE INHIBITORS, PROCESS FOR THEIR PREPARATION AND PHARMACEUTICAL COMPOSITIONS COMPRISING THEM

(75) Inventors: Giovanni Cervi, Como (IT); Matteo D'Anello, Novate Milanese (IT); Gianluca Mariano Enrico Papeo, Cernusco Lombardone (IT); Barbara Salom, Vedano al Lambro (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/482,626

(22) Filed: May 29, 2012

(65) Prior Publication Data

US 2012/0232085 A1     Sep. 13, 2012

Related U.S. Application Data

(63) Continuation of application No. 12/934,422, filed as application No. PCT/EP2009/053668 on Mar. 27, 2009, now Pat. No. 8,207,165.

(30) Foreign Application Priority Data

Mar. 28, 2008  (EP) .................................... 08153532

(51) Int. Cl.
*A61K 31/5355*    (2006.01)
*A61K 31/501*     (2006.01)
*C07D 413/14*     (2006.01)
*C07D 241/04*     (2006.01)

(52) U.S. Cl.
USPC .......... 514/233.2; 514/250; 544/115; 544/344

(58) Field of Classification Search
USPC ....................... 514/233.2, 250; 544/115, 344
See application file for complete search history.

(56) References Cited

FOREIGN PATENT DOCUMENTS

| WO | 00/44753 | | 8/2000 |
|----|----------|----|--------|
| WO | 02/10169 | A1 | 2/2002 |
| WO | 02/072584 | A2 | 9/2002 |
| WO | 2007/065820 | A1 | 6/2007 |

OTHER PUBLICATIONS

Golub et al. Science (1999), vol. 286 531-537.*
Lala et al. Cancer and Metastasis Reviews (1998), 17(1), 91-106.*
International Search Report dated Jan. 21, 2010 received from the European Patent Office.

* cited by examiner

*Primary Examiner* — Samantha Shterengarts
(74) *Attorney, Agent, or Firm* — Scully, Scott, Murphy & Presser, P.C.

(57) ABSTRACT

Compounds which are 3,4-dihydro-2H-pyrazino[1,2-a]indol-1-one derivatives or pharmaceutically acceptable salts thereof, their preparation process and pharmaceutical compositions comprising them are disclosed; these compounds are useful in the treatment of diseases caused by and/or associated with an altered protein kinase activity such as cancer, viral infection, prevention of AIDS development in HIV-infected individuals, cell proliferative disorders, autoimmune and neurodegenerative disorders; also disclosed is a process under Solid Phase Synthesis conditions for preparing the compounds of the invention and chemical libraries comprising a plurality of them.

2 Claims, No Drawings

3,4-DIHYDRO-2H-PYRAZINO[1,2-A]INDOL-1-ONE DERIVATIVES ACTIVE AS KINASE INHIBITORS, PROCESS FOR THEIR PREPARATION AND PHARMACEUTICAL COMPOSITIONS COMPRISING THEM

CROSS REFERENCE TO RELATED APPLICATIONS

The present application is a continuation of co-pending application having U.S. Ser. No. 12/934,422, filed on Sep. 24, 2012, which is a '371 of international application having Serial No. PCT/EP2009/053668, the contents of all of which are incorporated herein by reference.

The present invention relates to certain 8-amino derivatives of 3,4-dihydro-2H-pyrazino[1,2-a]indol-1-one compounds, which modulate the activity of protein kinases. The compounds of this invention are therefore useful in treating diseases caused by dysregulated protein kinase activity. The present invention also relates to methods for preparing these compounds, combinatorial libraries thereof, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis.

PKs are also implicated in inflammatory conditions and in the multiplication of viruses and parasites. PKs may also play a major role in the pathogenesis and development of neuro-degenerative disorders.

For a general reference to PKs malfunctioning or disregulation see, for instance, Current Opinion in Chemical Biology 1999, 3, 459-465 and Carcinogenesis 2008, 29, 1087-191.

3,4-Dihydro-2H-pyrazino[1,2-a]indol-1-one derivatives for the treatment of disorders of the central nervous system and obesity are disclosed in WO 2002/010169 and WO 2002/072584, all in the name of F. Hoffmann-La Roche A.-G. and Vernalis Research (Limited).

8-Oxy derivatives of 3,4-dihydro-2H-pyrazino[1,2-a]indol-1-one for the treatment of obesity are disclosed in WO2007/065820 in the name of F. Hoffmann-La Roche A.-G. 7-Carmaboyl-derivatives of 3,4-dihydro-2H-pyrazino[1,2-a]indol-1-one for the treatment of cytokine mediated diseases such as rheumatoid arthritis, inflammatory bowel disease and Alzheimer's disease are disclosed in US200627453, in the name of Boehringer Ingelheim Pharmaceuticals, Inc., USA.

The present inventors have now discovered that the new compounds of formula (I), described below, are kinase inhibitors and are thus useful in therapy as antitumor agents.

Accordingly, a first object of the present invention is to provide a 8-amino-3,4-dihydro-2H-pyrazino[1,2-a]indol-1-one compound represented by formula (I):

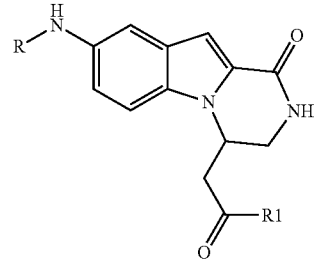

wherein
R is selected from the group consisting of $-R^a$, $-COR^a$, $-CONR^aR^b$, $-SO_2R^a$ and $-COOR^a$, and
R1 is a group $-NR^cR^d$ or $-OR^c$,
wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, heterocyclyl or heterocyclyl $C_1$-$C_6$ alkyl, aryl or aryl $C_1$-$C_6$ alkyl, heteroaryl or heteroaryl $C_1$-$C_6$ alkyl or, taken together with the nitrogen atom to which they are bonded, either $R^a$ and $R^b$ as well as $R^c$ and $R^d$ may form an optionally substituted 3 to 7 membered heterocyclyl or heteroaryl, optionally containing one additional heteroatom or heteroatomic group selected from S, O, N or NH,
and pharmaceutically acceptable salts thereof.

The present invention also provides methods of synthesizing the substituted 8-amino-3,4-dihydro-2H-pyrazino[1,2-a]indol-1-one compounds, represented by formula (I), prepared through a process consisting of standard synthetic transformations.

The present invention also provides a method for treating diseases caused by and/or associated with dysregulated protein kinase activity, particularly PLK family, ABL, AKT1, ALK, AUR1, AUR2, BRK, CDC7/DBF4, CDK2/CYCA, CHK1, CK2, EE2FK, EGFR1, ERK2, FAK, FGFR1, FLT3, GSK3beta, IGFR1, IKK2, IR, JAK2, JAK3, KIT, LCK, MAPKAPK2, MET, MPS1, NEK6, NIM1, P38alpha, PAK-4, PDGFR, PDK1, PERK, PIM1, PKAalpha, PKCbeta, PLK1, RET, B-RAF, STLK2, SULU1, TRKA, VEGFR2, VEGFR3, ZAP70.

A preferred method of the present invention is to treat a disease caused by and/or is associated with dysregulated protein kinase activity selected from the group consisting of cancer, viral infection, prevention of AIDS development in HIV-infected individuals, cell proliferative disorders, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma, neuroblastoma, glioma and schwannomas; other tumors, including mesothelioma, melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

In addition, the method of the present invention also provides tumor angiogenesis and metastasis inhibition, as well as treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent. Moreover the invention provides an in vitro method for inhibiting protein kinase activity which comprises contacting the said protein kinase with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, DNA damaging or intercalating agents, platin-based agents, alkylating agents, antimetabolite agents, hormonal agents, antihormonal agents such as antiestrogens, antiandrogens and aromatase inhibitors, immunological agents, interferon-type agents, cyclooxygenase inhibitors (e.g. COX-2 inhibitors), matrixmetalloprotease inhibitors, tyrosine kinase inhibitors, other kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, inhibitors of kinesins, therapeutic monoclonal antibodies, inhibitors of mTOR, histone deacetylase inhibitors, inhibitors of hypoxic response and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament. Moreover the invention provides the use of a compound of formula (I) or a pharmaceutically acceptable salt thereof, as defined above, in the manufacture of a medicament for treating diseases caused by and/or associated with an altered protein kinase activity.

Finally, the invention provides a compound of formula (I) or a pharmaceutically acceptable salt thereof, as defined above, for use in a method for treating diseases caused by and/or associated with an altered protein kinase activity.

Unless otherwise specified, when referring to the compounds of formula (I) per se as well as to any pharmaceutical composition thereof or to any therapeutic method of treatment comprising them, the present invention includes all the solvates, hydrates, complexes, metabolites, prodrugs, carriers, N-oxides and pharmaceutically acceptable salts of the compounds of this invention.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

"Hydrate" is a solvate wherein the solvent molecule is $H_2O$.

A "metabolite" of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

The term "prodrug", as employed herein, denotes a compound that is a drug precursor, which, upon administration to a subject, undergoes chemical conversion by metabolic or chemical processes to yield a compound of formula (I) or a salt and/or solvate thereof. A discussion of prodrugs is provided in T. Higuchi and V. Stella, Pro-drugs as Novel Delivery Systems (1987) Volume 14 of the A.C.S. Symposium Series, and in Bioreversible Carriers in Drug Design, (1987) Edward B. Roche, ed., American Pharmaceutical Association and Pergamon Press.

All forms of chiral isomers or other forms of isomers including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone.

In cases wherein compounds may exist in tautomeric forms, such as keto-enol tautomers, each tautomeric form is contemplated as being included within this invention whether existing in equilibrium or predominantly in one form.

In the present description, unless otherwise indicated, with the term "straight or branched $C_1$-$C_6$ alkyl" we intend any group such as, for instance, methyl, ethyl, n-propyl, isopropyl, n-butyl, isobutyl, sec-butyl, tert-butyl, n-pentyl, n-hexyl, and the like. With the term "straight or branched $C_2$-$C_6$ alkenyl" or "straight or branched $C_2$-$C_6$ alkynyl" we intend any of the unsaturated alkenyl or alkynyl groups with from 2 to 6 carbon atoms for instance including vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term "$C_3$-$C_6$ cycloalkyl" we intend, unless otherwise specified, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "aryl" we intend a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

With the term "heteroaryl" we intend aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the meanings provided to $R^a$, $R^b$, $R^c$ and $R^d$, any of the above groups may be further optionally substituted in any of their free positions by one or more groups, for instance 1 to 6 groups, selected from: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, cycloalkyl, cycloalkenyl, heterocyclyl, aryl, heteroaryl; amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfonyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

In the present description, unless otherwise specified, with the term "cyano" we intend a —CN residue.

With the term "nitro" we intend a —NO$_2$ group.

With the term "halogen" we intend a fluorine, chlorine, bromine or iodine atom.

With the term "polyfluorinated alkyl or alkoxy" we intend a straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the terms heterocyclyl-alkyl and cycloalkyl-alkyl stand for a straight or branched alkyl group being further substituted by a heterocyclic or cycloalkyl group, respectively, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, fumaric, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of formula (I) are the compounds wherein:

R1 is a group —NR$^c$R$^d$ and R$^c$ and R$^d$ are both hydrogen atoms or one of them is a hydrogen atom and the remaining one of R$^c$ or R$^d$ is a straight or branched $C_1$-$C_6$ alkyl or $C_2$-$C_6$ alkenyl group or it is an optionally substituted aryl or arylalkyl group.

Another preferred class of compounds of formula (I) are the compounds wherein:

R is a group R$^a$ wherein R$^a$ is hydrogen, or is a group —SO$_2$R$^a$ wherein R$^a$ is straight or branched $C_1$-$C_6$ alkyl or optionally substituted aryl or arylalkyl.

A further preferred class of compounds of formula (I) are the compounds wherein:

R is a group —COR$^a$ wherein R$^a$ is a straight or branched $C_1$-$C_6$ alkyl, cycloalkyl or optionally substituted aryl or arylalkyl group.

A more preferred class of compounds of formula (I) are the compounds wherein:

R is a group —CONR$^a$R$^b$ wherein one of R$^a$ and R$^b$ are hydrogen and the other is straight or branched $C_1$-$C_6$ alkyl, optionally substituted aryl or arylalkyl group.

For a reference to any specific compound of formula (I) of the invention, optionally in the form of pharmaceutically acceptable salts, see the experimental section.

The intermediate compound of formula (VII):

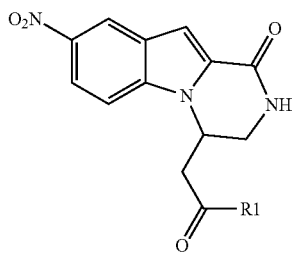

(VII)

wherein R1 is as defined above, is novel and hence represents a further object of the invention.

The present invention also provides a process for the preparation of a compound of formula (I) as defined above, characterized in that the process comprises:
a) hydrolysing under basic or acidic conditions the compound of formula (II):

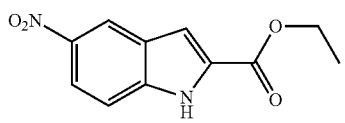

(II)

b) reacting the resultant compound of formula (III) or a salt thereof:

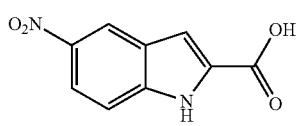

(III)

with 2,2-dimethoxy-ethylamine, after activation of the carboxyl group;
c) deprotecting under acidic conditions the resultant compound of formula (IV):

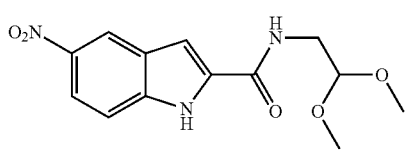

(IV)

d) reacting under basic conditions the resultant compound of formula (V):

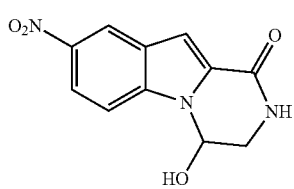

(V)

with a phosphonate of formula (VI):

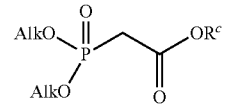

(VI)

wherein Alk is $C_1$-$C_6$ alkyl and $R^c$ is $C_1$-$C_6$ alkyl;
optionally converting the resultant compound of formula (VII):

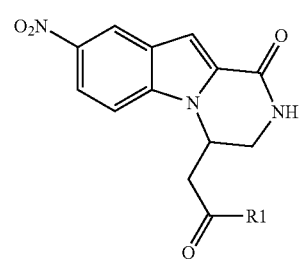

(VII)

wherein R1 represents $OR^c$ and $R^c$ is $C_1$-$C_6$ alkyl, into another compound of formula (VII) by replacing the —$OR^c$ group with a different group among those represented by R1;
e) reducing said compound of formula (VII) to give a compound of formula (I) or a salt thereof:

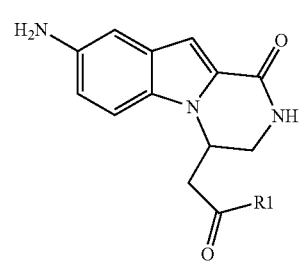

(I)

wherein R1 is $OR^c$ and $R^c$ is $C_1$-$C_6$ alkyl;
optionally separating the resultant compound of formula (I) into the single isomers; converting the resultant compound of formula (I) into a different compound of formula (I) by derivatising the amino moiety, and/or by replacing the group —$OR^c$ with a different group among those represented by R1, and/or into a pharmaceutically acceptable salt if desired.

The present invention further provides a process for the preparation of a compound of formula (I) as defined above, characterized in that the compound of formula (I) prepared in steps from a) to e) described above, is converted into another compound of formula (I) by derivatising the amino moiety, said derivatization being carried out by one or more of the following reactions:
f) reacting a compound of formula (I) wherein R is hydrogen and R1 is —$OR^c$ and $R^c$ is $C_1$-$C_6$ alkyl, according to any one of the alternative steps:
f.1) with an acid or an acyl halide of formula (VIII):

$R^aCOZ$ (VIII)

wherein R$^a$ is as defined above and Z is a halogen or a group —OH, to give a compound of formula (I):

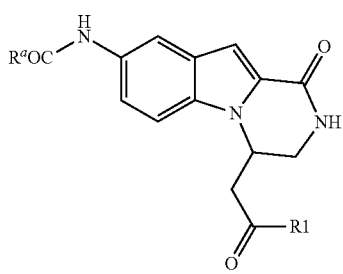

wherein R1 is —OR$^c$ and R$^c$ is C$_1$-C$_6$ alkyl and R$^a$ are as defined above; or f.2) with an isocyanate of formula (IX):

R$^a$NCO (IX)

wherein R$^a$ is as defined above, to give a compound of formula (I):

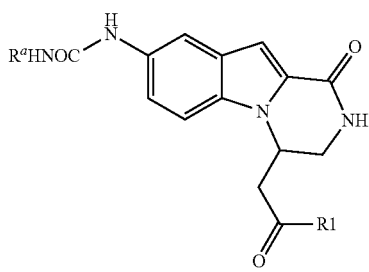

wherein R1 is —OR$^c$ and R$^c$ is C$_1$-C$_6$ alkyl and R$^a$ are as defined above; or f.3) with a sulphonyl halide of formula (X):

R$^a$SO$_2$Z' (X)

wherein R$^a$ is as defined above and Z' is a halogen, to give a compound of formula (I):

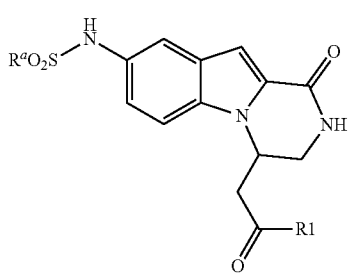

wherein R1 is —OR$^c$ and R$^c$ is C$_1$-C$_6$ alkyl and R$^a$ are as defined above; or f.4) with a halogen carbonate of formula (XI):

R$^a$OCOZ' (XI)

wherein R$^a$ and Z' are as defined above, to give a compound of formula (I):

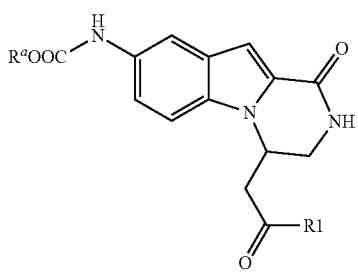

wherein R1 is —OR$^c$ and R$^c$ is C$_1$-C$_6$ alkyl and R$^a$ are as defined above; or f.5) with an amine of formula (XII):

HNR$^a$R$^b$ (XII)

wherein R$^a$ and R$^b$ are as defined above, in presence of a suitable chloroformate, to give a compound of formula (I):

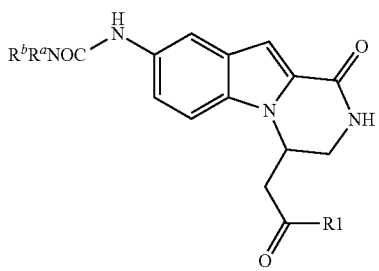

wherein R1 is —OR$^c$ and R$^c$ is C$_1$-C$_6$ alkyl, and R$^a$ and R$^b$ are as defined above; or (f.6) with a suitable aldehyde or ketone derivative of formula (XIII):

R$^a$—CO—R$^a$ (XIII)

wherein each of R$^a$, the same or different, are as defined above, to give a compound of formula (I):

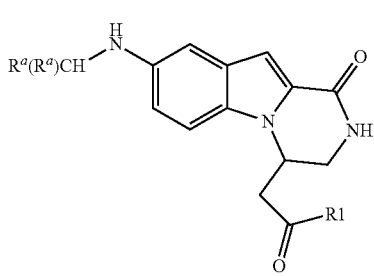

wherein R1 is —OR$^c$ and R$^c$ is C$_1$-C$_6$ alkyl and each of R$^a$, the same or different, are as defined above; or (f.7) with an halide of formula (XIV):

R$^a$—Z' (XIV)

wherein $R^a$ and Z' are as defined above, to give a compound of formula (I):

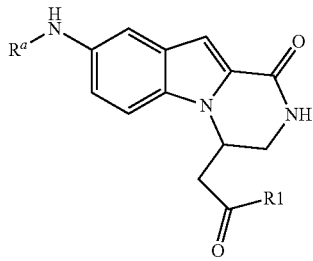

wherein R1 is —$OR^c$ and $R^c$ is $C_1$-$C_6$ alkyl and $R^a$ are as defined above;
optionally separating the resultant compound of formula (I) into the single isomers;
converting the resultant compound of formula (I) into a different compound of formula (I) by replacing the group —$OR^c$ with a different group among those represented by R1, and/or into a pharmaceutically acceptable salt if desired.

The present invention further provides a process for the preparation of a compound of formula (I) as defined above, characterized in that the compound of formula (I) is converted into another compound of formula (I), said conversion is carried out by one or more of the following reactions:

g.1) acid or basic hydrolysis of a compound of formula (I) wherein R1 is —$OR^c$ and $R^c$ is $C_1$-$C_6$ alkyl, to give the corresponding compound of formula (I) wherein R1 is —$OR^c$ and $R^c$ is hydrogen, or the corresponding salt;

g.2) transesterification of a compound of formula (I) wherein R1 is —$OR^c$ and $R^c$ is $C_1$-$C_6$ alkyl, by reactions with a compound of formula (XV):

$$R^c\text{—OH} \quad (XV)$$

to give the corresponding compound of formula (I) wherein R1 is —$OR^c$ and $R^c$ is a different $C_1$-$C_6$ alkyl;

g.3) aminolysis of a compound of formula (I) wherein $R_1$ is —$OR^c$ and $R^c$ is $C_1$-$C_6$ alkyl, by reaction with a compound of formula (XVI):

$$HNR^cR^d \quad (XVI)$$

to give the corresponding compound of formula (I) wherein R1 is —$NR^cR^d$;

g.4) esterification of a compound of formula (I) wherein R1 is a group —OH or its corresponding salt, by reactions with a compound of formula (XV) as defined above, to give the corresponding compound of formula (I) wherein R1 is —$OR^c$;

g.5) amidation of a compound of formula (I) wherein R1 is a group —OH or its corresponding salt, by reaction with a compound of formula (XVI) as defined above, to give the corresponding compound of formula (I) wherein R1 is —$NR^cR^d$.

The present invention further provides a process for the preparation of a compound of formula (I) as defined above, characterized in that the compound of formula (VII) as defined above, is converted into another compound of formula (VII), said conversions are carried out by one or more of the following reactions:

h.1) acid or basic hydrolysis of a compound of formula (VII) wherein R1 is —$OR^c$ and $R^c$ is $C_1$-$C_6$ alkyl, to give a compound of formula (VII) wherein R1 is —$OR^c$ and $R^c$ is hydrogen, or the corresponding salt;

h.2) transesterification of a compound of formula (VII) wherein R1 is —$OR^c$ and $R^c$ is $C_1$-$C_6$ alkyl, by reaction with a compound of formula (XV) as defined above, to give a compound of formula (VII) wherein R1 is —$OR^c$ and $R^c$ is a different $C_1$-$C_6$ alkyl;

h.3) amidation of a compound of formula (VII) wherein R1 is —$OR^c$ and $R^c$ is $C_1$-$C_6$ alkyl, by reaction with a compound of formula (XVI) as defined above, to give a compound of formula (VII) wherein R1 is —$NR^cR^d$;

h.4) esterification of a compound of formula (VII) wherein R1 is —$OR^c$ and $R^c$ is hydrogen, or the corresponding salt, by reaction with a compound of formula (XV) as defined above, to give a compound of formula (VII) wherein R1 is —$OR^c$ and $R^c$ is different from hydrogen;

h.5) amidation of a compound of formula (VII) wherein R1 is —$OR^c$ and $R^c$ is hydrogen, by reaction with a compound of formula (XVI) as defined above, to give a compound of formula (VII) wherein R1 is —$NR^cR^d$.

From all of the above, it is clear to the skilled person that if a compound of formula (I) or (VII), prepared according to the above processes comprehensive of any variant thereof, is obtained as an admixture of isomers, their separation into the single isomers of formula (I), carried out according to conventional techniques, is still within the scope of the present invention.

Likewise, the conversion of a compound of formula (I) into a pharmaceutically acceptable salt thereof or, alternatively, the conversion into the free compound (I) of a corresponding salt, according to procedures well-known in the art, is still within the scope of the invention.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared according to well-known methods. Likewise, the compounds of formula (II), (VI), (VIII), (IX), (X), (XI), (XII), (XIII), (XIV), (XV), (XVI), are known or easily obtained according to known methods, for a general reference see: Smith, Michael—March's Advanced Organic Chemistry: reactions mechanisms and structure—$5^{th}$ Edition, Michael B. Smith and Jerry March, John Wiley & Sons Inc., New York (NY), 2001.

According to step (a) of the process, the hydrolysis of the compound of formula (II) under basic or acidic conditions can be carried out in a variety of ways, according to conventional methods for hydrolysing esters derivatives. Preferably, the reaction is carried out in the presence of aqueous lithium hydroxide, methanol and tetrahydrofuran, at a temperature ranging from room temperature to about 90° C. and for a time from 4 hours to one day. According to the operative conditions being employed, the compound of formula (III) could be obtained either in its acidic form or, alternatively, as a salt. According to step (b) of the process, the conversion of the compound of formula (III) into the corresponding amido derivative of formula (IV), can be carried out in a variety of ways, according to conventional methods for obtaining amido derivatives from the corresponding acids. For example the reaction may be carried out by reaction with 2,2-dimethoxy-ethylamine after activation of the carboxylic function of the compound of formula (III) by reaction with thionyl chloride, oxalyl chloride or alternatively in the presence of a suitable condensing agent, for instance dicyclohexylcarbodiimide (DCC), 1-ethyl-3-(3'-dimethylaminopropyl)carbodiimide (EDC), O-benzotriazolyl-tetramethylisouronium tetrafluoroborate (TBTU) or benzotriazol-1-yloxy-tripyrrolidino-phosphonium hexafluorophosphate (PyBOP). Preferably, the reaction is carried out using thionyl chloride in dioxane as solvent and the isolated acyl chloride, by volatiles removal, is reacted with 2,2-dimethoxy-ethylamine under well-known Schotten-Baumann conditions.

According to step (c) of the process, the deprotection of the di-methyl acetal of the compound of formula (IV) can be carried out in a variety of ways, according to conventional methods for acetal removal. Preferably, the reaction is carried out in the presence of a suitable solvent, for instance in acetone and water, under acidic conditions, for instance in the presence of a mineral acid, preferably hydrochloric acid.

According to step (d) of the process, the reaction of the compound of formula (V) with compound of formula (VI) can be carried out in a variety of ways, according to conventional methods for Horner-Emmons reaction. Preferably, the reaction is carried out using different organic or inorganic bases such as lithium hydroxide in tetrahydrofuran and water or 1,8-diazabicyclo[5.4.0]undec-7-ene in acetonitrile with the trimethyl phosphonoacetate of formula (VI).

According to step (e) of the process, the reduction of the nitro group of the compound of formula (VII) to give a compound of formula (I), can be carried out in a variety of ways, according to conventional methods for reducing nitro group to the corresponding amino derivative. Preferably the reaction is carried out in the presence of tin (II) chloride in dimethylformamide (DMF) at room temperature for a time ranging from 4 to 24 hours.

According to any one of steps (f.1) to (f.7) the preparation of functionalized amino derivatives starting from the corresponding amine can be carried out in a variety of ways, according to conventional methods.

Preferably, according to step (f.1), (f.3) and (f.4) of the process, the compound of formula (I) is dissolved in a suitable solvent such as dichloromethane, dimethylformamide, tetrahydrofuran, dioxane or the like, and a suitable base such as triethylamine, diisopropylethylamine or sodium carbonate is added therein.

The compounds of general formula (VIII), (X) or (XI) are then added and the mixture stirred for a time of about 2 hours to about 15 hours, at a temperature ranging from about 20° C. to about 80° C. A suitable catalyst such as dimethylamino pyridine may be optionally used.

Preferably according to step (f.2) of the process, the reaction conditions are the same as above reported for steps (f.1), (f.3) and (f.4) except that the base may not be required. The compound of general formula (IX) is then added and the mixture stirred as reported above for steps (f.1), (f.3) and (f.4).

Preferably according to step (f.5) of the process, the compound of formula (I) is reacted with an amino derivative of formula (XII) after activation by reaction with a suitable chloroformate such as, for instance, 4-nitrophenylchloroformate. The reaction is carried out in a suitable solvent such as a halogenated hydrocarbon, preferably dichloromethane, in the presence of a base such as, for instance, diisopropylethylamine or triethylamine and by working at room temperature.

Preferably according to step (f.6) of the process, the compound of formula (I) is with reacted with an aldehyde or ketone derivative of formula (XIII). It is clear to the skilled man that by employing an aldehyde derivative of formula (XIII) wherein one of the two $R^a$ is a hydrogen atom, the corresponding derivatives wherein R is —$CH_2R^a$ are obtained. Likewise, by employing a ketone derivative, compounds having R as —$CH(R^a)R^a$ are obtained, wherein each $R^a$ is, independently from each other, as set forth above but other than hydrogen. The reaction can be carried out in a variety of ways, according to conventional methods for reductive amination. Preferably, the reaction is carried out by reaction with an aldehyde or ketone derivative of formula (XIII) in a suitable solvent such as tetrahydrofuran and after a time from 2 to 12 hours by addition of a reducing agent such as sodium cyanoborohydride or sodium triacetoxyborohydride.

Preferably according to step (f.7) of the process, the compound of formula (I) is reacted with an aromatic iodide or bromide of formula (XIV) in the presence of a suitable catalyst, for instance a palladium catalyst like palladium acetate or $Pd_2(dba)_3$, and of a suitable ligand. See, for a general reference to the above arylation reaction and operative conditions thereof also inclusive of solvents, catalysts and ligands, J. Am. Chem. Soc., (2003), 125, 6653-55; JOC (2001), 66, 2560-2565; and JOC (2002), 67, 6479-6486.

According to any one of steps (g.1) to (g.5) the conversion of a compound of formula (I) into another compound of formula (I) can be carried out in a variety of ways, according to conventional methods.

Preferably according to step (g.1) of the process, the hydrolysys of a compound of formula (I) wherein R1 is —$OCH_3$, to give the corresponding compound of formula (I) wherein R1 is —OH is carried out under acidic or basic conditions. Preferably, the reaction is carried out as described under step (a). According to the operative conditions being employed, the compound of formula (I) wherein R1 is —OH could be obtained either in its acidic form or, alternatively, as a salt.

Preferably according to step (g.2) of the process, the transesterification of a compound of formula (I) wherein R1 is —$OCH_3$, to give the corresponding compound of formula (I) wherein R1 is —$OR^c$ and $R^c$ is an alkyl different from methyl, is carried out by reaction with a compound of formula (XV) in an appropriate solvent, such as the compound of formula (XV) itself or dioxane at the refluxing temperature, optionally in the presence of a suitable metal based catalysts, like dibutylin oxide or titanium alkoxides such as, for instance, titanium (IV) ethoxide, titanium (IV) isopropoxide and the like.

Preferably according to step (g.3) of the process, the aminolysis of a compound of formula (I) wherein R1 is —$OCH_3$, to give the corresponding compound of formula (I) wherein R1 is —$NR^cR^d$ is carried out in an appropriate solvent such as dioxane or dichloromethane optionally in the presence of a suitable metal based catalysts, like trimethyl aluminium.

Preferably according to step (g.4) of the process, the esterification of a compound of formula (I) wherein R1 is a group —OH to give the corresponding compound of formula (I) wherein R1 is —$OR^c$ is carried out in the presence of a suitable condensing agent, for instance dicyclohexylcarbodiimide (DCC), 1-ethyl-3-(3'-dimethylaminopropyl)-carbodiimide (EDC), O-benzotriazolyltetramethylisouronium tetrafluoroborate (TBTU) or benzotriazol-1-yloxytripyrrolidinophosphonium hexafluorophosphate (PyBOP), in an appropriate solvent such as dichloromethane, dimethylformamide.

Preferably according to step (g.5) of the process, the amidation of a compound of formula (I) wherein R1 is a group —OH to give the corresponding compound of formula (I) wherein R1 is —$NR^cR^d$ can be carried out in a variety of ways, according to conventional methods for obtaining amido derivatives from the corresponding acids. Preferably, the reaction is carried out by reaction with compound of formula (XVI) after activation of the carboxylic function of the compound of formula (I) by reaction with thionyl chloride, oxalyl chloride or alternatively in the presence of a suitable condensing agent, for instance dicyclohexylcarbodiimide (DCC), 1-ethyl-3-(3'-dimethylaminopropyl)carbodiimide (EDC), O-benzotriazolyltetramethylisouronium tetrafluoroborate (TBTU) or benzotriazol-1-yloxytripyrrolidinophosphonium hexafluorophosphate (PyBOP), in an appropriate solvent such as dichloromethane, and/or dimethylformamide.

According to any one of steps (h.1) to (h.5) the conversion of a compound of formula (VII) into another compound of formula (VII) can be carried out in a variety of ways, according to conventional methods.

Preferably it is carried out as described under the steps from (g.1) to (g.5).

In addition to the above, the compounds of formula (I) may be advantageously prepared according to combinatorial chemistry techniques widely known in the art, by accomplishing the aforementioned reactions between the intermediates in a serial manner and by working under solid-phase-synthesis (SPS) conditions.

As an example, the intermediate carboxy ester derivatives of formula (VII), wherein R1 represents $OR^c$ and $R^c$ is $C_1$-$C_6$ alkyl, being obtained in step (d) of the above processes, can be first converted into the free carboxy acid derivative by means of hydrolysis carried out according to conventional methods, then easily supported onto a polymeric resin, for instance through the formation of a carboxamido group.

The intermediate thus supported may be subsequently reacted according to the remaining steps of the process.

The above synthetic pathway can be summarized as follows:

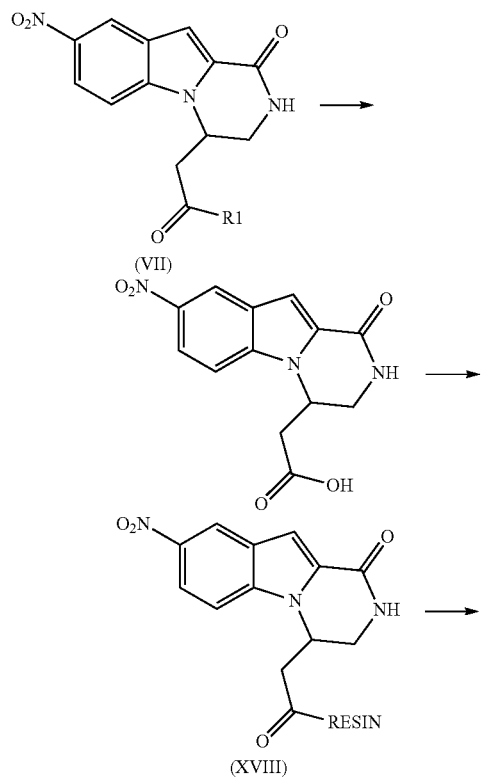

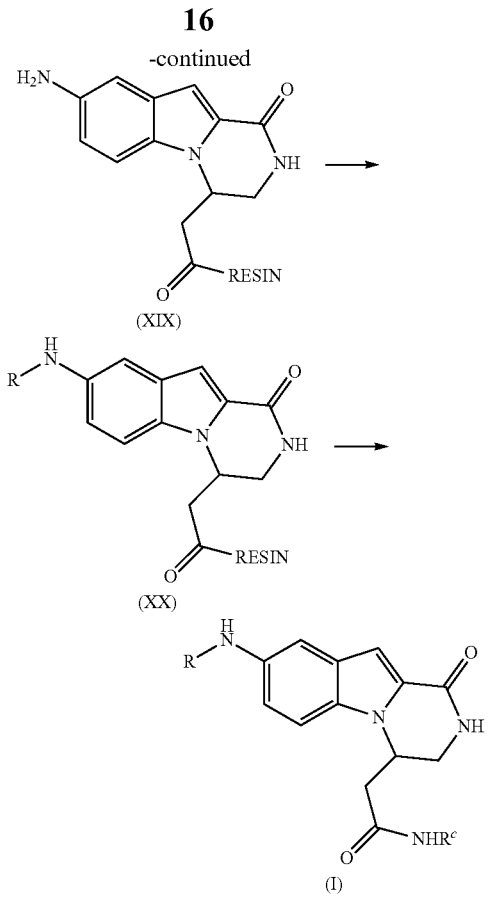

Any of the above reactions is carried out according to known methods, by working as formerly reported, and allows to obtain compounds of formula (I) as set forth above. Preferably, the above resin is a commercially available polystyrenic resin including, for instance, Wang resin, Trityl resin, Cl-trityl resin, Rink amide resin, Tentagel OH resin and derivatives thereof.

According to a preferred embodiment of the invention, the polystyrenic resin is a derivatized formyl polystyrenic resin which may be obtained by reacting a commercially available formyl polystyrenic resin, e.g. 4-(4-formyl-3-methoxyphenoxy)butyryl AM resin, with a suitable amino derivative under reductive conditions, for instance in the presence of sodium triacetoxyborohydride and derivatives thereof, substantially as follows:

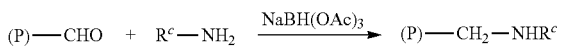

The reaction may be carried out in a suitable solvent such as tetrahydrofuran and in the presence of acetic acid.

The polymer-supported-amino derivatives thus obtained, particularly those, which are referable to as derivatized formyl polystyrenic resin above, are widely known in the art. In general, amines loaded onto formylpolystyrenic resins also known as Acid Sensitive MethoxyBenzaldehyde polystirene resins (AMEBA resin) are prepared by standard reductive amination in the presence of an excess of amine in TMOF/DCE and $NaBH(OAc)_3$ or AcOH/DMF and $NaCNBH_3$, for instance as reported in Tetrahedron Letters (1997), 38, 7151-7154; J. Am. Chem. Soc. (1998), 120, 5441; and Chem. Eur. J. (1999), 5, 2787.

Therefore, it is a further object of the present invention a process for preparing the compounds of formula (I), and the pharmaceutically acceptable salts thereof, which process comprises:

i) hydrolyzing under acid or basic conditions the compound of formula (VII) wherein R1 represents $OR^c$ and $R^c$ is $C_1$-$C_6$ alkyl;

j) reacting the resultant acid derivative with a derivatized formyl polystyrenic resin of formula (XVII):

(P)—$CH_2$—$NHR^c$          (XVII)

wherein (P) is the resin and $R^c$ is as defined above;

k) reacting of the resultant compound of formula (XVIII):

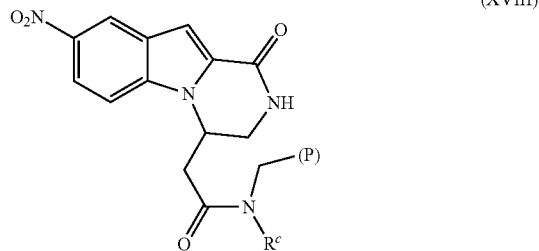

wherein (P) and $R^c$ are as described above, with a suitable reducing agent such as chromium (II) chloride, tetrabutylammonium hydrogen sulfide or tin (II) chloride; and l) reacting the resultant compound of formula (XIX):

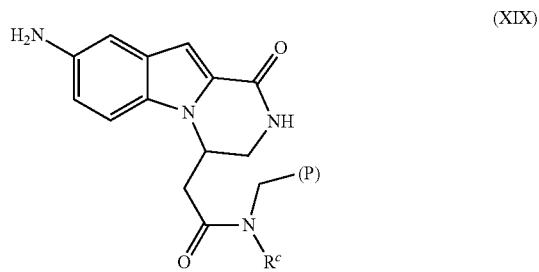

wherein (P) and $R^c$ are as described above, as described under any one of steps from (f.1) to (f.7);

m) cleaving the resin under acidic conditions from the resultant compound of formula (XX):

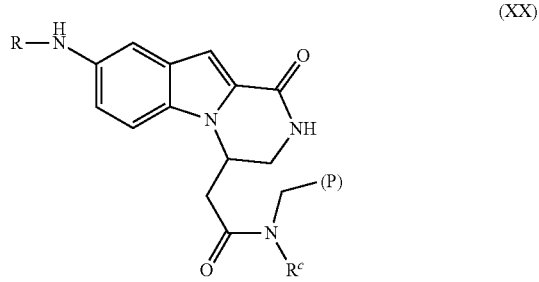

to give a compound of formula (I), wherein R is as defined above and R1 is —$NHR^c$, wherein $R^c$ is as defined above, optionally separating the resultant compound of formula (I) into the single isomers; converting the resultant compound of formula (I) into a different compound of formula (I) and/or into a pharmaceutically acceptable salt if desired.

According to step (i) of the process, the hydrolysis of a compound of formula (VII) wherein $R_1$ is —$OCH_3$, to give the corresponding compound of formula (VII) wherein R1 is —OH is carried out as described under step (h.1).

According to step (j) of the process, the reaction with the polystyrene resin is performed in a suitable solvent, for instance NMP, in the presence of diisopropylethylamine (DIPEA) and of a suitable condensing agent such as, for instance, 1-ethyl-3-(3'-dimethylaminopropyl)carbodiimide (EDC) or O-benzotriazolyl tetramethylisouronium tetrafluoroborate (TBTU).

According to step (k) of the process, the supported compound of formula (XVIII) is reduced to obtain the corresponding amino derivative; the reaction is carried out in the presence of tin (II) chloride in dimethylformamide (DMF) at room temperature for a time ranging from 4 to 24 hours.

According to step (l), the supported compound of formula (XIX) is optionally further reacted to give to a variety of compounds functionalised in position 5 of the 3,4-dihydro-2H-pyrazino[1,2-a]indol-1-one ring, as described under any one of steps from (f.1) to (f.7).

According to step (m), the cleavage of the resin is performed under acidic conditions in the presence of suitable acids such as, for instance, hydrochloric, trifluoroacetic, methanesulfonic or p-toluensulfonic acid. Preferably the reaction is carried out using trifluoroacetic acid in dichloromethane as solvent.

Clearly, by working according to combinatorial chemistry techniques as formerly indicated, a plurality of compounds of formula (I) may be obtained.

Hence, it is a further object of the present invention a library of two or more compounds of formula (I)

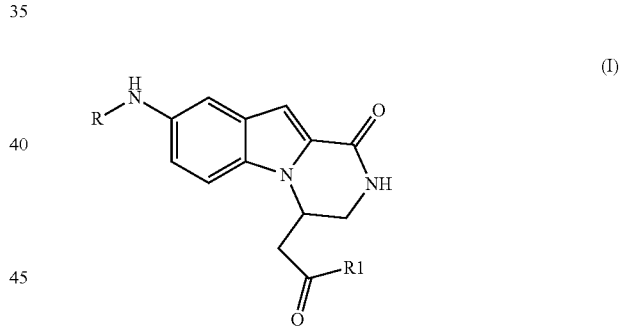

wherein

R is selected from the group consisting of —$R^a$, —$COR^a$, —$CONR^aR^b$, —$SO_2R^a$ and —$COOR^a$, and R1 is a group —$NR^cR^d$ or —$OR^c$, wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, heterocyclyl or heterocyclyl $C_1$-$C_6$ alkyl, aryl or aryl $C_1$-$C_6$ alkyl, heteroaryl or heteroaryl $C_1$-$C_6$ alkyl or, taken together with the nitrogen atom to which they are bonded, either $R^a$ and $R^b$ as well as $R^c$ and $R^d$ may form an optionally substituted 3 to 7 membered heterocyclyl or heteroaryl, optionally containing one additional heteroatom or heteroatomic group selected from S, O, N or NH, and pharmaceutically acceptable salts thereof.

According to a preferred embodiment of the invention, the aforementioned library comprises the compounds of formula (I) wherein $R_1$ is a group —$NR^cR^d$ and $R^c$ and $R^d$ are both hydrogen atoms or one of them is a hydrogen atom and the remaining one of $R^c$ or $R^d$ is a straight or branched $C_1$-$C_6$ alkyl or $C_2$-$C_6$ alkenyl group or it is an optionally substituted aryl or arylalkyl group.

Also preferred is a library of compounds of formula (I) wherein R is either a group $R^a$ with $R^a$ as a hydrogen atom or a group —$SO_2R^a$ with $R^a$ as a straight or branched $C_1$-$C_6$ alkyl group or optionally substituted aryl or arylalkyl group; and $R_1$ is as above defined. Also preferred is a library of compounds of formula (I) wherein R is a group —$COR^a$ with $R^a$ as a straight or branched $C_1$-$C_6$ alkyl, cycloalkyl or optionally substituted aryl or arylalkyl group.

Also preferred is a library of compounds of formula (I) wherein R is a group-$CONR^aR^b$ with one of $R^a$ and $R^b$ as a hydrogen atom and the other of $R^a$ and $R^b$ as a straight or branched $C_1$-$C_6$ alkyl, optionally substituted aryl or arylalkyl group.

For a general reference to the above libraries of compounds of formula (I) see the experimental section.

From all of the above, it is clear to the skilled person that once a library of 3,4-dihydro-2H-pyrazino[1,2-a]indol-1-one derivatives is thus prepared, for instance consisting of a few thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The inhibiting activity of putative kinase inhibitors and the potency of selected compounds is determined through a method of assay based on the use of the Kinase-Glo® Luminescent Kinase Assay (commercially available from Promega corporation and described in Koresawa, M. and Okabe, T. (2004) High-throughput screening with quantitation of ATP consumption: A universal non-radioisotope, homogeneous assay for protein kinase. *Assay Drug Dev. Technol.* 2, 153-60).

The depletion of ATP as a result of kinase activity can be monitored in a highly sensitive manner through the use of Kinase-Glo® or Kinase-Glo® Plus Reagent, which uses luciferin, oxygen and ATP as substrates in a reaction that produces oxyluciferin and light.

The short forms and abbreviations used herein have the following meaning:
BSA bovine serum albumine
Tris 2-Amino-2-(hydroxymethyl)-1,3-propanediol
Hepes N-(2-Hydroxyethyl)piperazine-N'-(2-ethanesulfonic acid)
DTT threo-1,4-Dimercapto-2,3-butanediol
THF tetrahydrofurane
MTBE methyl tertiary butyl ether
DIPEA diisopropylethylamine
PyBOP benzotriazol-1-yloxytris(pyrrolidino)phosphonium exafluorophosphate
TFA trifluoroacetic acid
TMOF trimethyl orto formate
DCE dichloroethane
DCM dichloromethane
DMF dimethylformammide
DMSO dimethylsulfoxide
KDa kiloDalton
mg milligram
µg microgram
ng nanogram
L liter
mL milliliter
µL microliter
M molar
mM millimolar
µM micromolar
nM nanomolar Kinase reaction conditions are target (enzyme) dependent and thus undergo individual adaptations. The Kinase-Glo® Luminescent Kinase Assay can be used with virtually any kinase and substrate combination.

Also the buffer conditions may vary depending on the kinase of interest (e.g for PKA a composition of 40 mM Tris pH 7.5, 20 mM MgCl2, 0.1 mg/ml BSA, in 50 µl final volume is used). Typically the range of ATP titration is 0.1 µM to 10 µM.

The optimal kinase substrate results in the greatest change in luminescence when comparing kinase reaction wells with no kinase wells.

The optimal amount of kinase is determined by making two fold serial dilutions across plates using the optimal amount of ATP and optimal kinase substrate. The optimal amount of kinase to use in subsequent compound screens and IC50 determinations is the amount required for luminescence to be within the linear range of the kinase titration curve (sigmoidal dose response).

Robotized Kinase-Glo® Assay

This assay was set up for the measurement of kinase activity and/or inhibition. It is homogeneous, suitable for all type of protein kinases, quick and radioactivity-free.

We established the assay in 384 well-plates: the test mix consisted of:
1) 3× Enzyme mix (done in Kinase Buffer 3×), 5 µl well
2) 3× substrate and ATP mix (done in ddH2O), 5 µl/well
3) 3× compound of formula (I) (diluted into ddH2O—3% DMSO)—5 µl/well)

As an outcome, the percentage of inhibition at 10 µM was evaluated for each compound tested: see below for compound dilution and assay scheme. Each enzyme had its own buffer constitution, substrate type and concentration. Incubation time instead was 90 min for all targets.

Test compounds were received as a 1 mM solution in 100% DMSO into 96 well plates. The plates were diluted to 30 µM in ddH$_2$O, 3% DMSO; 4 plates are reorganized in 384 well plate by dispensing 5 µl of each 96wp into the four quadrants of a 384wp. In well P23 and P24 the internal standard inhibitor staurosporine was added.

Assay Scheme

Test plates were first added with 5 µl of the compound dilution (30 µM, corresponding to 3× dilution) and then loaded onto a robotized station together with one reservoir for the Enzyme mix (3×) and one for the ATP mix (3×), specific for each target under study.

To start the assay, the robot aspirated 5 µl of ATP/Substrate mix, made an air gap inside the tips (5 µl) and aspirated 5 µl of Enzyme mix. The subsequent dispensation into the test plates allowed the kinase reaction to start after 3 cycles of mixing, done by the robot itself by up and down pipetting. At this point, the correct concentration was restored for all reagents.

The robot incubated the plates for 90 minutes at room temperature, and then stopped the reaction by pipetting 15 µl of Kinase-Glo® reagent into the reaction mix. Three cycles of mixing were done immediately after the addition of the reagent.

The principle of the Kinase-Glo® technique is the presence in the reagent mixture of oxygen, luciferin and luciferase enzyme: in the presence of ATP, remaining from the kinase reaction, oxi-luciferin is produced with the emission of light, directly dependent on the amount of ATP. For optimal performances of this technique, the kinase reaction should utilize at least 15-20% of the available ATP.

After another 60 minutes of incubation to stabilize the luminescent signal, the plates were read on a ViewLux® instrument. Data were analyzed using the software package Assay Explorer® that provided percent inhibition data.

As example herein are reported the assay conditions used for testing the compounds of formula (I) against ALKtide YFF APCo kinase;

ATP concentration: 1 µM

Enzyme concentration: 100 nM

Reaction buffer: Hepes 50 mM pH 7.5, MgCl2 5 mM, MnCl2 1 mM, DTT 1 mM, NaOVO3 3 uM, 0.2 mg/ml BSA Assay procedure: add 5 ul compound of formula (I) (3×), add 5 µl ATP/S mix(3×) in buffer 1×; add 5 µl enzyme in buffer 2×+3×BSA; for the blank, add 5 µl buffer2×+3× BSA without enzyme. After 90 minutes of incubation, add 15 µl/well of Kinase-Glo reagent. After 60-90 minutes of incubation to stabilize the luminescent signal, the plates are read on a ViuwLux instrument.

Some representative compounds of the invention of formula (I), such as compound A23-M-B63, A23-M-B55 and A20-M-B14 (for the meanings of the codes, see the Examples section), at a dosage of 10 µM have been found to have a % inhibition >25% when tested in the method described above.

So far, the novel compounds of the invention are unexpectedly endowed with a kinase inhibitory activity against a selected panel of kinases, and are thus particularly advantageous, in therapy, against proliferative disorders associated with an altered kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

General Methods

Flash Chromatography was performed on silica gel (Merck grade 9395, 60A). The high-pressure liquid chromatography retention times (HPLC: r.t. values) were determined by:

HPLC Method 1A and 1B:

A Waters Alliance LC mod. 2795 equipped with a variable UV detector mod 2487, a Chemiluminescence Nitrogen detector (CLND, Antek 8060) and a Waters ZQ2000 mass detector (ESI interface) was used in this application. The total flow was splitted and distributed to the three detectors at a fixed ratio (64:15:21 UV:MS:CLND). The liquid chromatograph was equipped with a 30×3.0 mm I.D. column (Waters) xBridge C18, 3.5 um particles), thermostated at 50° C. Two mobile phases were used: phase A was 0.05% w/v formic acid (1 mL/L of 50% formic acid Fluka 09676 in highly purified water) and phase B was 70/25/5 (v/v/v) MeOH/iPrOH/H2O containing 0.035% w/v of formic acid (700 uL/L of 50% formic acid Fluka 09676).

A 5 μL volume of 1 mM nominal sample solution in DMSO was injected (sequential, partial loop mode with no air gaps) and a generic reversed phase gradient analysis was carried out at 0.8 mL/min into either a fast variant (method 1A) or a slower one (method 1B), as indicated in the following table:

| Method 1A | | Method 1B | |
|---|---|---|---|
| tR (min) | phase B (%) | tR (min) | phase B (%) |
| 0.00 | 0 | 0.00 | 0 |
| 5.00 | 100 | 8.00 | 100 |
| 5.70 | 100 | 9.00 | 100 |
| 5.71 | 0 | 9.01 | 0 |
| 6.3 | stop time | 9.6 | stop time |
| 7.9 | total analysis time (*) | 11.2 | total analysis time (*) |

(*) between consecutive injections

The UV detector was operated at 220 nm, 5 Hz sampling rate. The MS device was operated at 3.2 kV capillary voltage, 30 V cone, 2 V extractor, 0.5 V RF lens, 400 L/hr desolvation flow, 100 L/hr cone flow, 100° C. source temperature, 150° C. desolvation temperature, ESI(+) full scan 120-1200 amu acquisition, at 1.7 Hz sampling rate. The CLND detector was operated at 1050° C. furnace temp, 280 mL/min inlet oxygen flow, 80 mL/min inlet argon, 25 mL/min make-up argon, 30 mL/min ozone, 28 ton vacuum, 750 V PMT voltage, PMT chamber at +10° C., sensitivity high, select 5, 4 Hz sampling rate.

HPLC Method 2:

Instrumentation: Waters 2790 HPLC system equipped with a 996 Waters PDA detector and Micromass mod. ZQ 2000 single quadrupole mass spectrometer, equipped with an electrospray (ESI) ion source.

Chromatographic condition: Waters X Terra RP18 (4,6×50 mm, 3.5 μm) column; Mobile phase A was ammonium acetate 5 mM buffer (pH 5.2 with acetic acid)/acetonitrile 95:5, and Mobile phase B was H$_2$O/acetonitrile (5:95). Gradient from 10 to 90% B in 8 minutes, hold 100% B for 2 minutes. PDA channels extracted at 220 nm and 254 nm. Flow rate 1 ml/min. Injection volume 10 μl. Full scan, mass range from 100 to 800 amu. Capillary voltage was 3.5 kV; source temp. was 120° C.; cone was 14 V. Retention times (HPLC r.t.) are given in minutes at 220 nm or at 254 nm. Mass is given as m/z ratio.

When necessary, the compounds have been purified by preparative HPLC on a Waters X-Bridge Prep Shield RP18 (19×100 mm, 5 μm) column or a Phenomenex Gemini C18 (21.2×250 mm, 10 μm) column, using a Waters FractionLynx Autopurification System equipped with a 996 Waters PDA detector and a Micromass mod. ZQ single quadrupole mass spectrometer, electron spray ionization, positive mode. Mobile phase A was water 0.05% NH3/acetonitrile 95:5, and Mobile phase B was acetonitrile. Gradient from 10 to 90% B in 8 min or 15 min Flow rate 20 ml/min.

$^1$H-NMR spectrometry was performed on a Bruker AVANCE 400 MHz single bay instrument with gradients. It is equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

The compounds of formula (I), having an asymmetric carbon atom and obtained as racemic mixture, were resolved by HPLC separation on chiral columns. In particular, for example, preparative columns CHIRALPACK® AD, CHIRALPACK® AS, CHIRALCELL® OJ can be used.

As formerly indicated, several compounds of formula (I) of the invention have been synthesized in parallel, according to combinatorial chemistry techniques.

In this respect, some compounds thus prepared have been conveniently and unambiguously identified, as per the coding system of tables III, VI, V and VI together with HPLC retention time (methods 1 and 2) and mass.

Each code, which identifies a single specific compound of formula (I), consists of three units A-M-B.

A represents any substituent R$_1$— [see formula (I)] and is attached to the rest of the 3,4-dihydro-2H-pyrazino[1,2-a] indol-1-one moiety through the carbon atom of the carbonyl group so as to get 3,4-dihydro-2H-pyrazino[1,2-a]indol-1-one derivatives; each A radical (substituent) is represented in the following table I.

B represents any substituent R—[see formula (I)] and is attached to the rest of the 3,4-dihydro-2H-pyrazino [1,2-a] indol-1-one moiety through the nitrogen atom of the NH group so as to get 3,4-dihydro-2H-pyrazino[1,2-a]indol-1-one derivatives being substituted in position 8; each B radical (substituent) is represented in the following table II.

M refers to the central core of the divalent 3,4-dihydro-2H-pyrazino[1,2-a]indol-1-one moiety being substituted at the carbonyl group by groups A and in position 8 (through the NH group) by groups B, substantially as follows:

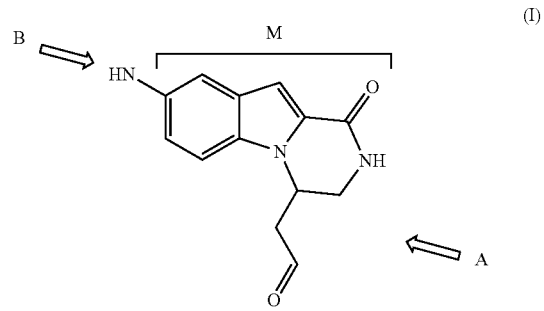

(I)

For ease of reference, each A or B groups of tables I and II has been identified with the proper chemical formula also indicating the point of attachment with the rest of the molecule M.

Just as an example, the compound A2-M-B2 of table III (entry 1) represents an 3,4-dihydro-2H-pyrazino[1,2-a]indol-1-one M being substituted in position 8 by the group B2 (through the NH group), and by the group A2 through the CO group; likewise, the compound A4-M-09 of table IV (entry 780) represents an 3,4-dihydro-2H-pyrazino[1,2-a]indol-1-one M being substituted in position by the group B9 (through the NH group), and by the group A4 through the CO group, as follows:

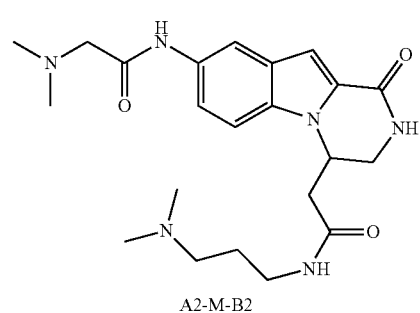

A2-M-B2

-continued
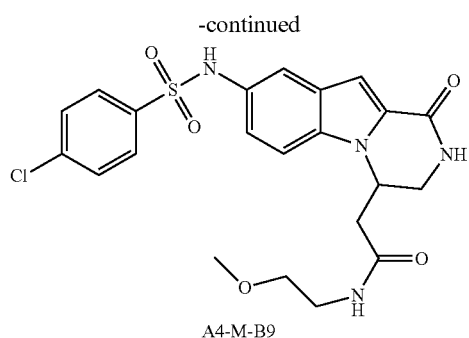
A4-M-B9
TABLE I
| A groups | |
|---|---|
| Fragment | CODE |
|  | A1 |
|  | A2 |
|  | A3 |
|  | A4 |
|  | A5 |
|  | A6 |
|  | A7 |
|  | A8 |
|  | A9 |
|  | A10 |
|  | A11 |
TABLE I-continued
| A groups | |
|---|---|
| Fragment | CODE |
|  | A12 |
|  | A13 |
|  | A14 |
|  | A15 |
|  | A16 |
|  | A17 |
|  | A18 |
|  | A19 |
|  | A20 |
|  | A21 |
|  | A22 |
|  | A23 |

TABLE I-continued
A groups
| Fragment | CODE |
|---|---|
| 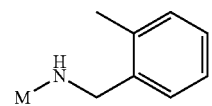 | A24 |
| 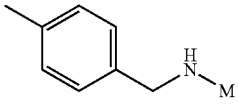 | A25 |
| 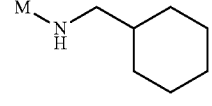 | A26 |
| 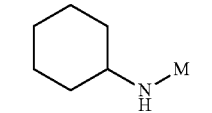 | A27 |
| 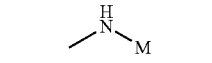 | A28 |
TABLE II
B groups
| Fragment | CODE |
|---|---|
| 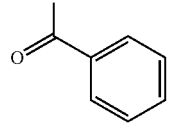 | B1 |
| 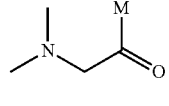 | B2 |
| 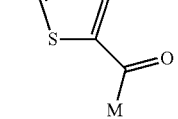 | B3 |
| 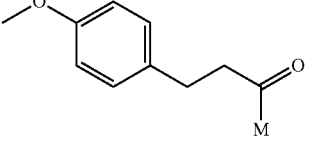 | B4 |
| 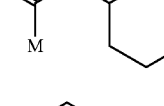 | B5 |
| 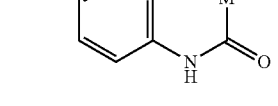 | B6 |
TABLE II-continued
B groups
| Fragment | CODE |
|---|---|
| 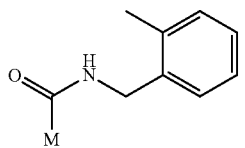 | B7 |
| 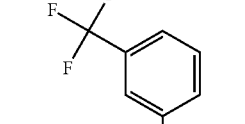 | B8 |
| 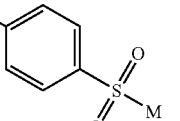 | B9 |
| 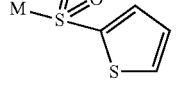 | B10 |
| 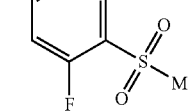 | B11 |
| 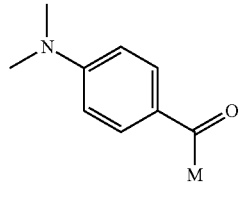 | B12 |
| 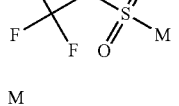 | B13 |
| 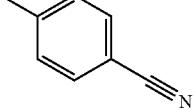 | B14 |
| 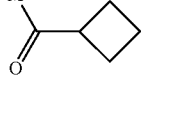 | B15 |

TABLE II-continued

B groups

| Fragment | CODE |
|---|---|
| (cyclopropyl C(=O)-M) | B16 |
| (3,4-dimethylphenyl C(=O)-M) | B17 |
| (2-fluorophenyl C(=O)-M) | B18 |
| (CH₃-S(=O)₂-M) | B19 |
| (thiophene-2-yl C(=O)-M) | B20 |
| (4-methylphenyl S(=O)₂-M) | B21 |
| (2-methylphenyl C(=O)-M) | B22 |
| (3-methylphenyl C(=O)-M) | B23 |
| (4-methylphenyl C(=O)-M) | B24 |
| (cyclohexyl C(=O)-M) | B25 |
| (2-ethylbutanoyl-M) | B26 |
| (3-methylbutanoyl-M) | B27 |
| (2,5-dimethylphenyl C(=O)-M) | B28 |
| (3-cyanophenyl C(=O)-M) | B29 |
| (2-chloro-6-fluorophenyl C(=O)-M) | B30 |
| (2,6-difluorophenyl C(=O)-M) | B31 |
| (ethyl S(=O)₂-M) | B32 |
| (2-methylbutanoyl-M) | B33 |
| (3,5-difluorophenyl C(=O)-M) | B34 |
| (cyclohexylacetyl-M) | B35 |

TABLE II-continued
| B groups | |
|---|---|
| Fragment | CODE |
| 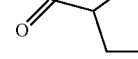 | B36 |
| 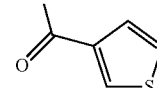 | B37 |
| 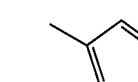 | B38 |
| 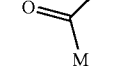 | B39 |
| 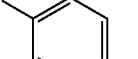 | B40 |
|  | B41 |
| 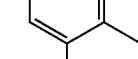 | B42 |
| 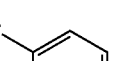 | B43 |
| 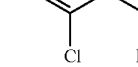 | B44 |
| 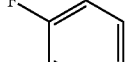 | B45 |
TABLE II-continued
| B groups | |
|---|---|
| Fragment | CODE |
| | B46 |
| | B47 |
| | B48 |
| | B49 |
| | B50 |
| | B51 |
| | B52 |
| | B53 |
| | B54 |
| | B55 |
| | B56 |

TABLE II-continued

B groups

| Fragment | CODE |
|---|---|
| (N-methylcarbamoyl) | B57 |
| (2-methoxyethylcarbamoyl) | B58 |
| (3-fluoro-4-methylbenzoyl) | B59 |
| (1-ethyl-1H-pyrazol-5-ylcarbonyl) | B60 |
| (1-ethyl-1H-pyrazol-3-ylcarbonyl) | B61 |
| (3-fluoro-4-methylphenylsulfonyl) | B62 |
| (3,5-difluorophenylsulfonyl) | B63 |
| (pyridin-3-ylcarbonyl) | B64 |
| (2,4-difluorobenzoyl) | B65 |
| (3,5-dimethylbenzoyl) | B66 |
| (2-fluoro-5-chlorobenzoyl) | B67 |
| (1-methyl-1H-pyrazol-5-ylcarbonyl) | B68 |
| (benzylsulfonyl) | B69 |
| (4-bromophenylacetyl) | B70 |
| (3,3-dimethylbutanoyl) | B71 |
| (3-trifluoromethylphenylsulfonyl) | B72 |
| (N-benzylcarbamoyl) | B73 |
| (N-propylcarbamoyl) | B74 |

TABLE II-continued

B groups

| Fragment | CODE |
|---|---|
| M—CH2—cyclohexyl | B75 |
| M—CH2—(3-bromophenyl) | B76 |

Preparation of 5-nitro-1H-indole-2-carboxylic acid (III)

LiOH.H2O (1.06 g, 46.2 mmol, 2.1 eq.) was added to a suspension of 5-nitro-1H-indole-2-carboxylic acid ethyl ester (II) (5.15 g, 22 mmol, 1 eq.) in THF/MeOH/H2O 1:1:2 (180 ml). The final suspension turned to dark yellow and was stirred at 25° C. After 30 min the solubilization was complete and total conversion was achieved after 6 hours. The reaction mixture was cooled to 0° C. and quenched with HCl 2N until the solution reached pH 5. Organic volatiles were removed under reduced pressure and the white precipitate was filtered and dried to give the compound of formula (III). Yield=4.53 g (quantitative). Same procedure on 50 g scale afforded 42.2 g of the compound of formula (III) (96% yield).

LCMS (HPLC Method 2): m/z 205 [M−H]− @ r.t. 2.58 min
$^1$H NMR (400 MHz, DMSO-d$_6$) δ ppm 2.59 (dd, J=15.91, 5.67 Hz, 1 H) 2.82 (dd, J=15.97, 8.29 Hz, 1 H) 3.58 (dd, J=12.86, 5.67 Hz, 1 H) 3.89 (dd, J=13.35, 4.08 Hz, 1 H) 5.17-5.23 (m, 1 H) 7.36 (s, 1 H) 7.80 (d, J=9.15 Hz, 1 H) 8.15 (dd, J=9.15, 2.32 Hz, 1 H) 8.27 (d, J=5.12 Hz, 1 H) 8.72 (d, J=2.32 Hz, 1 H) 12.58 (br. s., 1 H).

Preparation of 5-nitro-1H-indole-2-carboxylic acid (2,2-dimethoxy-ethyl)-amide (IV)

Thionyl chloride (8 ml, 110 mmol, 5 eq.) was added to a suspension of the compound of formula (III) (4.53 g, 22 mmol, 1 eq.) in dry dioxane (50 ml). The final suspension was refluxed in dry atmosphere (CaCl2 valve) for 2 h, and the reaction turned to a light brown solution while proceeding. The reaction was cooled to 25° C. and organic volatiles were removed under reduced pressure, then dry toluene (25 ml) was added and removed under vacuum, this operation was repeated twice. The brown residue (22 mmol, 1 eq.) was added portion wise to a cooled solution at 0° C. of NaHCO$_3$ (3.7 g, 43.95 mmol, 2 eq.) and 2,2-dimethoxy-ethylamine (2.39 ml, 21.97 mmol, 1 eq.) in dioxane/water 4:1 (100 ml), the suspension was stirred for 2 hours at rt. Organic volatiles were removed under reduced pressure and the yellow precipitate was filtered and dried to give 5-nitro-1H-indole-2-carboxylic acid (2,2-dimethoxy-ethyl)-amide (IV). Yield=5.80 g (90%).

Same procedure on 42.2 g scale afforded 52.75 g of a compound of formula (IV)(82% yield).

LCMS (HPLC Method 2): m/z 294 [M+H]+ @ r.t. 4.46 min. $^1$H NMR (400 MHz, DMSO-d$_6$) δ ppm 3.31 (s, 6 H) 3.40 (t, J=5.73 Hz, 2 H) 4.53 (t, J=5.49 Hz, 1 H) 7.43 (d, J=1.46 Hz, 1 H) 7.57 (d, J=9.02 Hz, 1 H) 8.07 (dd, J=9.02, 2.32 Hz, 1 H) 8.70 (d, J=2.32 Hz, 1 H) 8.80 (t, J=6.04 Hz, 1 H) 12.30 (s, 1 H).

Preparation of 4-hydroxy-8-nitro-3,4-dihydro-2H-pyrazino[1,2-a]indol-1-one (V)

HCl 2N (13.75 ml, 27.5 mmol, 2.5 eq.) was added to a solution of the compound of formula (IV) (3 g, 11 mmol, 1 eq.) in acetone (200 ml), the final solution was stirred at 25° C. for 48 h. The solution was dried under reduced pressure affording the compound of formula (V) as yellow solid that was used in the subsequent step without further purification. Same procedure on 30 g scale proceeded smoothly. Typical yield: 97%.

Warning: on higher scale a careful drying step until constant weight is mandatory in order to avoid that residual HCl interferes in the following step.

LCMS (HPLC Method 2): m/z 246 [M−H]− @ r.t. 3.1 min (broad peak).

Preparation of (8-nitro-1-oxo-1,2,3,4-tetrahydropyrazino[1,2-a]indol-4-yl)-acetic acid methyl ester (VII)

LiOH*H$_2$O (509 mg, 12.14 mmol, 1.5 eq.) was added to a solution of trimethyl phosphono acetate (VI) (1.28 ml, 8.90 mmol, 1.2 eq.), to the compound of formula (V) (2.0 g, 8.09 mmol, 1 eq.) and water (4.4 ml, 240 mmol, 30 eq.) in THF (100 ml) and the solution was stirred at 25° C. for 4 hours, then organic volatiles were removed under reduced pressure and the crude residue was used in the next step without further purification, after addition of 100 ml of water.

On higher scale (110 mol) the reaction was worse (low conversion) for the mentioned above residue of HCl.

LCMS (HPLC Method 2): m/z 304 [M+H]+ @ r.t. 3.96 min. $^1$H NMR (on isolated product) (400 MHz, DMSO-d6) δ ppm 2.68 (dd, J=15.61, 6.22 Hz, 1 H) 2.92 (dd, J=15.49, 7.44 Hz, 1 H) 3.51 (s, 3 H) 3.58 (ddd, J=13.29, 5.37, 1.10 Hz, 1 H) 3.90 (dd, J=13.41, 4.15 Hz, 1 H) 5.25 (dt, J=6.83, 3.66 Hz, 1 H) 7.36 (s, 1 H) 7.75 (d, J=9.15 Hz, 1 H) 8.17 (dd, J=9.27, 2.32 Hz, 1 H) 8.28 (d, J=5.00 Hz, 1 H) 8.72 (d, J=2.20 Hz, 1 H).

Preparation of (8-nitro-1-oxo-1,2,3,4-tetrahydropyrazino[1,2-a]indol-4-yl)-acetic acid (VII)

LiOH*H$_2$O (408 mg, 9.72 mmol, 1.2 eq.) was added to aqueous solution of the crude of example 4 and the resultant suspension was stirred at 25° C. for 4 hours. The brown suspension was filtered. The dark brown mother solution was quenched with HCl 2N until pH 5 was reached (yellow precipitate), organic volatiles were removed under reduced pressure and the yellow precipitate was filtered. The crude material was stirred with acetone (20 ml/g of crude) for 12 hours then the undissolved material was filtered and dried under reduced pressure (light yellow solid). Yields: 1.2 g of the acid derivative of formula (VII) (50% over two steps) 89% UV purity @254 nm.

Same procedure on higher scale afforded the compound of formula III with average yields of 35% over two steps and 90% UV purity @254 nm, the main impurity is the starting material of example 4.

LCMS (HPLC Method 2): m/z 288 [M−H]− @ r.t. 2.62 min. $^1$H NMR (400 MHz, DMSO-d$_6$) δ ppm 2.59 (dd, J=15.91, 5.67 Hz, 1 H) 2.82 (dd, J=15.97, 8.29 Hz, 1 H) 3.58 (dd, J=12.86, 5.67 Hz, 1 H) 3.89 (dd, J=13.35, 4.08 Hz, 1 H) 5.17-5.23 (m, 1 H) 7.36 (s, 1 H) 7.80 (d, J=9.15 Hz, 1 H) 8.15 (dd, J=9.15, 2.32 Hz, 1 H) 8.27 (d, J=5.12 Hz, 1 H) 8.72 (d, J=2.32 Hz, 1 H) 12.58 (br. s., 1 H).

General Procedure: Loading of Allylamine (Corresponding to Fragment A7 of Table I) onto Acid Sensitive Methoxy Benzaldehyde Polystyrene Resin (AMEBA II Resin).

4-(4-formyl-3-methoxyphenoxy)butyryl aminomethyl resin (copolystyrene-1% DVB) (6.0 g, 5.88 mmol, 0.98 mmol/g, 1 eq.) was suspended in dry THF (60 ml) and allylamine (29.4 mmol, 5 eq.) was added. The resultant suspension was shaken at 25° C. for 2 h. Then acetic acid (1.68 ml, 29.4 mmol, 5 eq.) and NaBH(AcO)₃ (3.12 g, 14.7 mmol, 3 eq.) were added and the final suspension was shaken for 16 h at 25° C. The resin was rinsed with THF (2 cycles), MeOH (2 cycles), DCM (2 cycles), MeOH (2 cycles), DMF (2 cycles) and DCM (3 cycles) then dried in nitrogen flux.

Loading of the 3,4-dihydro-2h-pyrazino[1,2-a]indol-1-one scaffold onto the resin prepared above

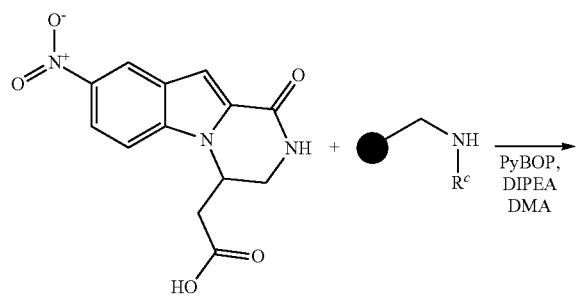

A solution of the acid derivative of formula (VII) (57 mg, 0.2 mmol, 2 eq), DIPEA (0.068 ml, 0.39 mmol, 4 eq.), PyBOP (102.75 mg, 0.2 mmol, 2 eq.) in dry DMA (2.0 ml) was stirred for 30 min then was added to resin of example 6 (0.1 mmol, 1 eq.) and the final suspension was shaken for 20 h at 25° C. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then air dried.

Reduction of the Nitro Group

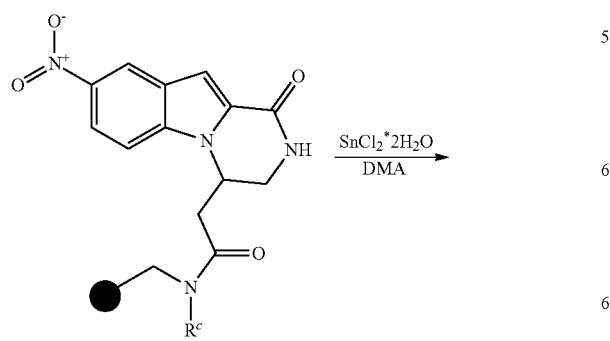

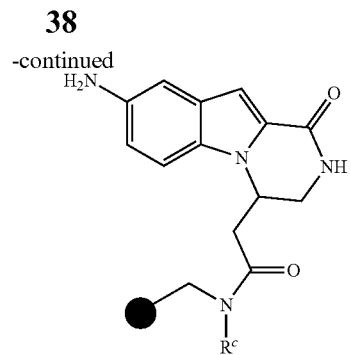

The resin of formula (XVIII) (0.1 mmol, 1 eq.) was suspended in a 2M solution of $SnCl_2 \cdot 2H_2O$ in DMF (1.5 ml). The final compound of formula (XIX) in suspension was shaken for 48 hours at 25° C. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then dried in nitrogen flux. The above resin bound 3,4-dihydro-2h-pyrazino[1,2-a]indol-1-one was further reacted according to the alternative steps below so as to get carboxamido, sulfonamido, ureido and amino derivatives.

Example 1

Preparation of A28-M-B1

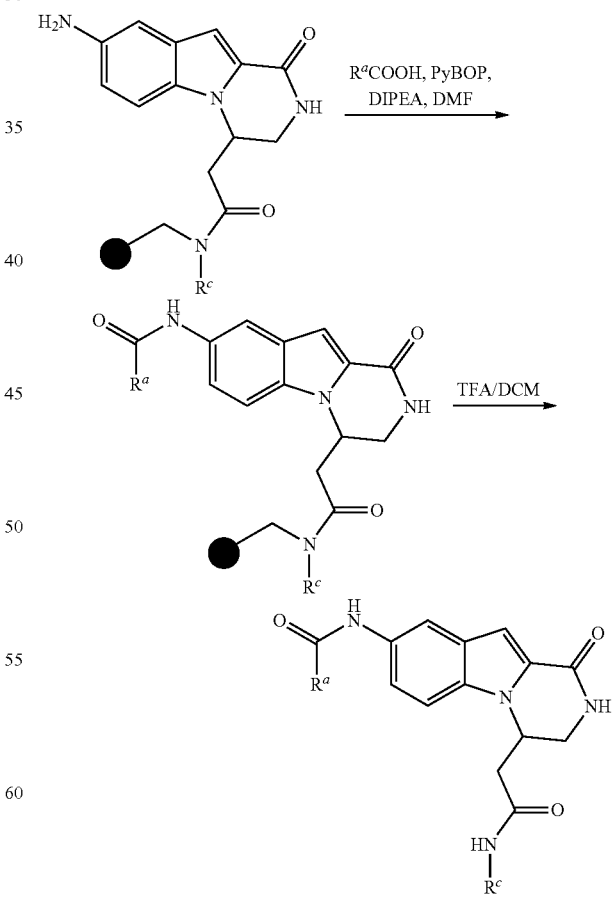

A carboxylic acid of formula (VIII), wherein $R^a$ corresponds to the fragment B1 of table II, (0.3 mmol, 3 eq.), was added to a the resin of example 8 wherein $R^c$ corresponds to the fragment A28 of table I, in solution of DIPEA (68.5 μl, 0.4 mmol, 4 eq.) and PyBOP (156 mg, 0.3 mmol, 3 eq.) in dry DMF (2.5 ml) and the solution was stirred for 30 min then was added to the resin of example 8 (0.1 mmol, 1 eq.) and shaken at 25° C. in a reactor (Quest 210™ or Miniblocks™). The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then air dried. The Resin (0.1 mmol, 1 eq.) was suspended in a solution of TFA/DCM 1:1 (2 ml) and shaken for 2 h at 25° C. The solution phase was collected and the resin was rinsed with DCM (collected as well), and a second cycle was performed. The final washing was performed with MeOH. All the collected were dried under reduced pressure affording compound A28-M-B1 (see entry 754 of table III below).

LCMS (HPLC Method 1A): m/z 377 [M+H]$^+$ @ r.t. 2.41 min. $^1$H NMR (400 MHz, DMSO-d$_6$) δ ppm 9.62 (s, 1H), 8.07 (s, 1H), 8.03 (d, J=4.9 Hz, 1H), 7.92 (t, J=5.6 Hz, 1H), 7.36-7.47 (m, 2H), 7.00 (s, 1H), 4.85-5.14 (m, 1H), 3.83 (dd, J=13.2, 4.3 Hz, 1H), 3.48 (dd, J=12.8, 5.6 Hz, 1H), 3.09 (s, 2H), 2.85-3.03 (m, 2H), 2.31 (s, 6H), 2.20 (br. s., 8H), 1.27-1.51 (m, 2H).

Following the procedure described in example 9 and by using any proper reactant as per the process of the invention that is, by supporting any suitable amine onto the resin, by acylating the amino function in position 8 of the 3,4-dihydro-2H-pyrazino[1,2-a]indol-1-one moiety with any suitable carboxylic acid derivative and by finally carrying out resin cleavage, the following compounds of table III were also prepared.

TABLE III

| Entry | Compound | HPLC Method | HPLC tR (min) | [M + H]+ |
|---|---|---|---|---|
| 1 | A2-M-B2 | 1B | 0.49 | 429 |
| 2 | A2-M-B3 | 1B | 3.02 | 468 |
| 3 | A2-M-B4 | 1B | 3.09 | 506 |
| 4 | A3-M-B2 | 1B | 0.49 | 457 |
| 5 | A3-M-B12 | 1B | 3.15 | 519 |
| 6 | A3-M-B4 | 1B | 3.16 | 534 |
| 7 | A4-M-B2 | 1B | 0.53 | 402 |
| 8 | A4-M-B3 | 1B | 4.31 | 441 |
| 9 | A4-M-B12 | 1B | 4.26 | 464 |
| 10 | A4-M-B4 | 1B | 4.36 | 479 |
| 11 | A5-M-B2 | 1B | 2.47 | 448 |
| 12 | A5-M-B3 | 1B | 5.38 | 487 |
| 13 | A5-M-B12 | 1B | 5.35 | 510 |
| 14 | A5-M-B4 | 1B | 5.39 | 525 |
| 15 | A6-M-B2 | 1B | 2.37 | 414 |
| 16 | A6-M-B3 | 1B | 5.35 | 453 |
| 17 | A6-M-B12 | 1B | 5.33 | 476 |
| 18 | A6-M-B4 | 1B | 5.36 | 491 |
| 19 | A7-M-B2 | 1B | 0.55 | 384 |
| 20 | A7-M-B3 | 1B | 4.54 | 423 |
| 21 | A7-M-B12 | 1B | 4.48 | 446 |
| 22 | A7-M-B4 | 1B | 4.57 | 461 |
| 23 | A8-M-B4 | 1B | 3.15 | 506 |
| 24 | A10-M-B14 | 1A | 2.58 | 472 |
| 25 | A10-M-B15 | 1A | 2.49 | 425 |
| 26 | A10-M-B16 | 1A | 2.24 | 411 |
| 27 | A10-M-B17 | 1A | 3.22 | 475 |
| 28 | A10-M-B18 | 1A | 2.7 | 465 |
| 29 | A10-M-B20 | 1A | 2.55 | 453 |
| 30 | A10-M-B22 | 1A | 2.77 | 461 |
| 31 | A10-M-B23 | 1A | 2.98 | 461 |
| 32 | A10-M-B24 | 1A | 2.98 | 461 |
| 33 | A10-M-B25 | 1A | 3.06 | 453 |
| 34 | A10-M-B26 | 1A | 2.82 | 441 |
| 35 | A10-M-B27 | 1A | 2.63 | 427 |
| 36 | A10-M-B28 | 1A | 3.11 | 475 |
| 37 | A10-M-B29 | 1A | 2.57 | 472 |
| 38 | A10-M-B30 | 1A | 2.66 | 499 |
| 39 | A10-M-B31 | 1A | 2.54 | 483 |
| 40 | A10-M-B33 | 1A | 2.58 | 427 |
| 41 | A10-M-B34 | 1A | 3.1 | 483 |
| 42 | A10-M-B35 | 1A | 3.33 | 467 |
| 43 | A10-M-B36 | 1A | 2.76 | 439 |
| 44 | A10-M-B37 | 1A | 2.55 | 453 |
| 45 | A10-M-B38 | 1A | 2.74 | 467 |
| 46 | A10-M-B39 | 1A | 3.1 | 483 |
| 47 | A10-M-B40 | 1A | 3.11 | 475 |
| 48 | A10-M-B41 | 1A | 2.91 | 499 |
| 49 | A10-M-B42 | 1A | 2.83 | 499 |
| 50 | A11-M-B33 | 1A | 2.68 | 385 |
| 51 | A10-M-B43 | 1A | 2.59 | 427 |
| 52 | A10-M-B44 | 1A | 2.22 | 441 |
| 53 | A10-M-B45 | 1A | 2.26 | 498 |
| 54 | A10-M-B46 | 1A | 2.71 | 481 |
| 55 | A10-M-B47 | 1A | 2.1 | 399 |
| 56 | A10-M-B48 | 1A | 2.71 | 427 |
| 57 | A10-M-B49 | 1A | 2.36 | 413 |
| 58 | A10-M-B50 | 1A | 2.33 | 413 |
| 59 | A10-M-B51 | 1A | 2.85 | 465 |
| 60 | A10-M-B52 | 1A | 1.88 | 385 |
| 61 | A10-M-B54 | 1A | 2.86 | 465 |
| 62 | A10-M-B59 | 1A | 3.19 | 479 |
| 63 | A10-M-B60 | 1A | 2.47 | 465 |
| 64 | A10-M-B61 | 1A | 2.44 | 465 |
| 65 | A12-M-B14 | 1A | 2.46 | 513 |
| 66 | A12-M-B15 | 1A | 2.37 | 466 |
| 67 | A12-M-B16 | 1A | 2.14 | 452 |
| 68 | A12-M-B17 | 1A | 3.08 | 516 |
| 69 | A12-M-B64 | 1A | 1.96 | 489 |
| 70 | A12-M-B20 | 1A | 2.43 | 494 |
| 71 | A12-M-B22 | 1A | 2.63 | 502 |
| 72 | A11-M-B34 | 1A | 3.22 | 441 |
| 73 | A12-M-B24 | 1A | 2.83 | 502 |
| 74 | A12-M-B25 | 1A | 2.88 | 494 |
| 75 | A12-M-B26 | 1A | 2.67 | 482 |
| 76 | A11-M-B35 | 1A | 3.46 | 425 |
| 77 | A12-M-B28 | 1A | 2.96 | 516 |
| 78 | A11-M-B36 | 1A | 2.87 | 397 |
| 79 | A12-M-B30 | 1A | 2.54 | 540 |
| 80 | A12-M-B31 | 1A | 2.41 | 524 |
| 81 | A12-M-B33 | 1A | 2.45 | 468 |
| 82 | A12-M-B65 | 1A | 2.72 | 524 |
| 83 | A12-M-B34 | 1A | 2.96 | 524 |
| 84 | A12-M-B35 | 1A | 3.19 | 508 |
| 85 | A12-M-B36 | 1A | 2.62 | 480 |
| 86 | A12-M-B66 | 1A | 3.16 | 516 |
| 87 | A12-M-B37 | 1A | 2.43 | 494 |
| 88 | A12-M-B38 | 1A | 2.61 | 508 |
| 89 | A12-M-B39 | 1A | 2.95 | 524 |
| 90 | A12-M-B40 | 1A | 2.96 | 516 |
| 91 | A12-M-B41 | 1A | 2.76 | 540 |
| 92 | A12-M-B43 | 1A | 2.46 | 468 |
| 93 | A12-M-B46 | 1A | 2.57 | 523 |
| 94 | A12-M-B47 | 1A | 2 | 440 |
| 95 | A12-M-B48 | 1A | 2.57 | 468 |
| 96 | A12-M-B49 | 1A | 2.25 | 454 |
| 97 | A12-M-B50 | 1A | 2.2 | 454 |
| 98 | A12-M-B51 | 1A | 2.71 | 506 |
| 99 | A13-M-B14 | 1A | 2.62 | 430 |
| 100 | A13-M-B15 | 1A | 2.54 | 383 |
| 101 | A13-M-B16 | 1A | 2.28 | 369 |
| 102 | A13-M-B17 | 1A | 3.31 | 433 |
| 103 | A13-M-B18 | 1A | 2.77 | 423 |
| 104 | A13-M-B64 | 1A | 2.06 | 406 |
| 105 | A13-M-B20 | 1A | 2.6 | 411 |
| 106 | A13-M-B22 | 1A | 2.85 | 419 |
| 107 | A13-M-B23 | 1A | 3.06 | 419 |
| 108 | A13-M-B24 | 1A | 3.04 | 419 |
| 109 | A13-M-B25 | 1A | 3.12 | 411 |
| 110 | A13-M-B26 | 1A | 2.89 | 399 |
| 111 | A13-M-B27 | 1A | 2.7 | 385 |
| 112 | A13-M-B28 | 1A | 3.19 | 433 |
| 113 | A13-M-B29 | 1A | 2.62 | 430 |
| 114 | A13-M-B30 | 1A | 2.72 | 457 |

TABLE III-continued

| Entry | Compound | HPLC Method | HPLC tR (min) | [M + H]+ |
|---|---|---|---|---|
| 115 | A13-M-B31 | 1A | 2.58 | 441 |
| 116 | A13-M-B33 | 1A | 2.63 | 385 |
| 117 | A13-M-B34 | 1A | 3.19 | 441 |
| 118 | A13-M-B35 | 1A | 3.43 | 425 |
| 119 | A13-M-B36 | 1A | 2.83 | 397 |
| 120 | A13-M-B66 | 1A | 3.39 | 433 |
| 121 | A13-M-B37 | 1A | 2.61 | 411 |
| 122 | A13-M-B38 | 1A | 2.81 | 425 |
| 123 | A13-M-B39 | 1A | 3.16 | 441 |
| 124 | A13-M-B40 | 1A | 3.19 | 433 |
| 125 | A13-M-B41 | 1A | 2.98 | 457 |
| 126 | A13-M-B42 | 1A | 2.88 | 457 |
| 127 | A13-M-B67 | 1A | 3.22 | 457 |
| 128 | A13-M-B43 | 1A | 2.63 | 385 |
| 129 | A13-M-B44 | 1A | 2.24 | 399 |
| 130 | A13-M-B45 | 1A | 2.3 | 456 |
| 131 | A13-M-B46 | 1A | 2.77 | 439 |
| 132 | A13-M-B47 | 1A | 2.12 | 357 |
| 133 | A13-M-B48 | 1A | 2.78 | 385 |
| 134 | A13-M-B49 | 1A | 2.4 | 371 |
| 135 | A13-M-B50 | 1A | 2.37 | 371 |
| 136 | A13-M-B51 | 1A | 2.91 | 423 |
| 137 | A13-M-B54 | 1A | 2.92 | 423 |
| 138 | A13-M-B59 | 1A | 3.26 | 437 |
| 139 | A13-M-B68 | 1A | 2.31 | 409 |
| 140 | A13-M-B60 | 1A | 2.52 | 423 |
| 141 | A13-M-B61 | 1A | 2.5 | 423 |
| 142 | A14-M-B14 | 1A | 3 | 478 |
| 143 | A14-M-B15 | 1A | 2.96 | 431 |
| 144 | A14-M-B16 | 1A | 2.69 | 417 |
| 145 | A14-M-B17 | 1A | 3.62 | 481 |
| 146 | A14-M-B18 | 1A | 3.14 | 471 |
| 147 | A14-M-B20 | 1A | 2.99 | 459 |
| 148 | A14-M-B22 | 1A | 3.22 | 467 |
| 149 | A14-M-B23 | 1A | 3.41 | 467 |
| 150 | A14-M-B24 | 1A | 3.39 | 467 |
| 151 | A14-M-B25 | 1A | 3.48 | 459 |
| 152 | A14-M-B26 | 1A | 3.28 | 447 |
| 153 | A14-M-B28 | 1A | 3.53 | 481 |
| 154 | A14-M-B29 | 1A | 2.99 | 478 |
| 155 | A14-M-B30 | 1A | 3.09 | 505 |
| 156 | A14-M-B31 | 1A | 2.95 | 489 |
| 157 | A14-M-B33 | 1A | 3.05 | 433 |
| 158 | A14-M-B34 | 1A | 3.55 | 489 |
| 159 | A14-M-B35 | 1A | 3.73 | 473 |
| 160 | A14-M-B66 | 1A | 3.7 | 481 |
| 161 | A14-M-B37 | 1A | 3.01 | 459 |
| 162 | A14-M-B38 | 1A | 3.18 | 473 |
| 163 | A14-M-B39 | 1A | 3.52 | 489 |
| 164 | A14-M-B40 | 1A | 3.52 | 481 |
| 165 | A14-M-B41 | 1A | 3.35 | 505 |
| 166 | A14-M-B42 | 1A | 3.26 | 505 |
| 167 | A14-M-B67 | 1A | 3.55 | 505 |
| 168 | A14-M-B44 | 1A | 2.65 | 447 |
| 169 | A14-M-B45 | 1A | 2.68 | 504 |
| 170 | A14-M-B52 | 1A | 2.28 | 391 |
| 171 | A14-M-B54 | 1A | 3.3 | 471 |
| 172 | A14-M-B59 | 1A | 3.58 | 485 |
| 173 | A15-M-B14 | 1A | 2.83 | 444 |
| 174 | A15-M-B15 | 1A | 2.78 | 397 |
| 175 | A15-M-B16 | 1A | 2.51 | 383 |
| 176 | A15-M-B17 | 1A | 3.5 | 447 |
| 177 | A15-M-B18 | 1A | 2.99 | 437 |
| 178 | A15-M-B20 | 1A | 2.82 | 425 |
| 179 | A15-M-B22 | 1A | 3.06 | 433 |
| 180 | A15-M-B23 | 1A | 3.26 | 433 |
| 181 | A15-M-B24 | 1A | 3.25 | 433 |
| 182 | A15-M-B25 | 1A | 3.33 | 425 |
| 183 | A15-M-B26 | 1A | 3.13 | 413 |
| 184 | A11-M-B66 | 1A | 3.43 | 433 |
| 185 | A15-M-B29 | 1A | 2.83 | 444 |
| 186 | A15-M-B30 | 1A | 2.93 | 471 |
| 187 | A15-M-B31 | 1A | 2.8 | 455 |
| 188 | A15-M-B33 | 1A | 2.87 | 399 |
| 189 | A15-M-B34 | 1A | 3.4 | 455 |
| 190 | A15-M-B35 | 1A | 3.62 | 439 |
| 191 | A11-M-B37 | 1A | 2.64 | 411 |
| 192 | A15-M-B37 | 1A | 2.84 | 425 |
| 193 | A15-M-B38 | 1A | 3.02 | 439 |
| 194 | A15-M-B39 | 1A | 3.37 | 455 |
| 195 | A15-M-B40 | 1A | 3.38 | 447 |
| 196 | A15-M-B41 | 1A | 3.2 | 471 |
| 197 | A15-M-B42 | 1A | 3.1 | 471 |
| 198 | A15-M-B67 | 1A | 3.41 | 471 |
| 199 | A15-M-B44 | 1A | 2.45 | 413 |
| 200 | A15-M-B45 | 1A | 2.5 | 470 |
| 201 | A15-M-B52 | 1A | 2.09 | 357 |
| 202 | A15-M-B54 | 1A | 3.14 | 437 |
| 203 | A15-M-B59 | 1A | 3.46 | 451 |
| 204 | A16-M-B14 | 1A | 2.91 | 456 |
| 205 | A16-M-B15 | 1A | 2.87 | 409 |
| 206 | A16-M-B16 | 1A | 2.6 | 395 |
| 207 | A16-M-B17 | 1A | 3.57 | 459 |
| 208 | A16-M-B18 | 1A | 3.07 | 449 |
| 209 | A16-M-B64 | 1A | 2.33 | 432 |
| 210 | A16-M-B20 | 1A | 2.91 | 437 |
| 211 | A16-M-B22 | 1A | 3.15 | 445 |
| 212 | A16-M-B23 | 1A | 3.35 | 445 |
| 213 | A16-M-B24 | 1A | 3.33 | 445 |
| 214 | A16-M-B25 | 1A | 3.42 | 437 |
| 215 | A16-M-B26 | 1A | 3.21 | 425 |
| 216 | A16-M-B27 | 1A | 3.03 | 411 |
| 217 | A16-M-B28 | 1A | 3.45 | 459 |
| 218 | A16-M-B29 | 1A | 2.91 | 456 |
| 219 | A16-M-B30 | 1A | 3.01 | 483 |
| 220 | A16-M-B31 | 1A | 2.87 | 467 |
| 221 | A16-M-B33 | 1A | 2.97 | 411 |
| 222 | A16-M-B34 | 1A | 3.49 | 467 |
| 223 | A16-M-B35 | 1A | 3.69 | 451 |
| 224 | A16-M-B36 | 1A | 3.14 | 423 |
| 225 | A16-M-B66 | 1A | 3.64 | 459 |
| 226 | A16-M-B37 | 1A | 2.93 | 437 |
| 227 | A16-M-B38 | 1A | 3.11 | 451 |
| 228 | A16-M-B39 | 1A | 3.47 | 467 |
| 229 | A16-M-B40 | 1A | 3.47 | 459 |
| 230 | A16-M-B41 | 1A | 3.28 | 483 |
| 231 | A16-M-B42 | 1A | 3.18 | 483 |
| 232 | A16-M-B67 | 1A | 3.49 | 483 |
| 233 | A16-M-B43 | 1A | 2.98 | 411 |
| 234 | A16-M-B44 | 1A | 2.54 | 425 |
| 235 | A16-M-B45 | 1A | 2.59 | 482 |
| 236 | A16-M-B46 | 1A | 3.07 | 465 |
| 237 | A16-M-B47 | 1A | 2.42 | 383 |
| 238 | A16-M-B48 | 1A | 3.09 | 411 |
| 239 | A16-M-B49 | 1A | 2.74 | 397 |
| 240 | A16-M-B50 | 1A | 2.7 | 397 |
| 241 | A16-M-B51 | 1A | 3.22 | 449 |
| 242 | A16-M-B52 | 1A | 2.16 | 369 |
| 243 | A16-M-B54 | 1A | 3.22 | 449 |
| 244 | A16-M-B59 | 1A | 3.53 | 463 |
| 245 | A11-M-B38 | 1A | 2.84 | 425 |
| 246 | A16-M-B61 | 1A | 2.78 | 449 |
| 247 | A17-M-B14 | 1A | 2.74 | 468 |
| 248 | A17-M-B17 | 1A | 3.39 | 471 |
| 249 | A11-M-B39 | 1A | 3.21 | 441 |
| 250 | A18-M-B14 | 1A | 3.15 | 492 |
| 251 | A18-M-B15 | 1A | 3.14 | 445 |
| 252 | A18-M-B16 | 1A | 2.88 | 431 |
| 253 | A18-M-B17 | 1A | 3.73 | 495 |
| 254 | A18-M-B18 | 1A | 3.28 | 485 |
| 255 | A18-M-B20 | 1A | 3.15 | 473 |
| 256 | A18-M-B22 | 1A | 3.35 | 481 |
| 257 | A18-M-B23 | 1A | 3.55 | 481 |
| 258 | A18-M-B25 | 1A | 3.62 | 473 |
| 259 | A18-M-B26 | 1A | 3.44 | 461 |
| 260 | A11-M-B40 | 1A | 3.21 | 433 |
| 261 | A11-M-B41 | 1A | 3.02 | 457 |
| 262 | A18-M-B30 | 1A | 3.24 | 519 |
| 263 | A11-M-B42 | 1A | 2.91 | 457 |
| 264 | A18-M-B33 | 1A | 3.23 | 447 |
| 265 | A18-M-B34 | 1A | 3.68 | 503 |
| 266 | A18-M-B35 | 1A | 3.85 | 487 |
| 267 | A18-M-B66 | 1A | 3.81 | 495 |
| 268 | A18-M-B37 | 1A | 3.17 | 473 |

TABLE III-continued

| Entry | Compound | HPLC Method | HPLC tR (min) | [M + H]+ |
|---|---|---|---|---|
| 269 | A18-M-B38 | 1A | 3.31 | 487 |
| 270 | A18-M-B39 | 1A | 3.65 | 503 |
| 271 | A11-M-B67 | 1A | 3.24 | 457 |
| 272 | A18-M-B41 | 1A | 3.47 | 519 |
| 273 | A18-M-B42 | 1A | 3.4 | 519 |
| 274 | A18-M-B67 | 1A | 3.66 | 519 |
| 275 | A11-M-B43 | 1A | 2.68 | 385 |
| 276 | A18-M-B45 | 1A | 2.86 | 518 |
| 277 | A18-M-B52 | 1A | 2.49 | 405 |
| 278 | A18-M-B54 | 1A | 3.45 | 485 |
| 279 | A18-M-B59 | 1A | 3.71 | 499 |
| 280 | A4-M-B15 | 1A | 2.33 | 399 |
| 281 | A4-M-B16 | 1A | 2.1 | 385 |
| 282 | A4-M-B17 | 1A | 3.09 | 449 |
| 283 | A4-M-B18 | 1A | 2.57 | 439 |
| 284 | A4-M-B64 | 1A | 1.9 | 422 |
| 285 | A4-M-B20 | 1A | 2.39 | 427 |
| 286 | A4-M-B22 | 1A | 2.63 | 435 |
| 287 | A4-M-B23 | 1A | 2.86 | 435 |
| 288 | A4-M-B24 | 1A | 2.83 | 435 |
| 289 | A4-M-B25 | 1A | 2.89 | 427 |
| 290 | A4-M-B26 | 1A | 2.65 | 415 |
| 291 | A4-M-B27 | 1A | 2.48 | 401 |
| 292 | A4-M-B28 | 1A | 2.96 | 449 |
| 293 | A4-M-B29 | 1A | 2.43 | 446 |
| 294 | A4-M-B30 | 1A | 2.52 | 473 |
| 295 | A4-M-B31 | 1A | 2.4 | 457 |
| 296 | A4-M-B33 | 1A | 2.42 | 401 |
| 297 | A4-M-B34 | 1A | 2.96 | 457 |
| 298 | A4-M-B35 | 1A | 3.21 | 441 |
| 299 | A4-M-B36 | 1A | 2.61 | 413 |
| 300 | A11-M-B44 | 1A | 2.28 | 399 |
| 301 | A4-M-B37 | 1A | 2.4 | 427 |
| 302 | A4-M-B38 | 1A | 2.6 | 441 |
| 303 | A4-M-B39 | 1A | 2.93 | 457 |
| 304 | A4-M-B40 | 1A | 2.97 | 449 |
| 305 | A4-M-B41 | 1A | 2.76 | 473 |
| 306 | A4-M-B42 | 1A | 2.67 | 473 |
| 307 | A4-M-B67 | 1A | 3 | 473 |
| 308 | A4-M-B43 | 1A | 2.43 | 401 |
| 309 | A4-M-B44 | 1A | 2.08 | 415 |
| 310 | A4-M-B46 | 1A | 2.56 | 455 |
| 311 | A4-M-B47 | 1A | 1.96 | 373 |
| 312 | A4-M-B48 | 1A | 2.56 | 401 |
| 313 | A4-M-B49 | 1A | 2.21 | 387 |
| 314 | A4-M-B50 | 1A | 2.17 | 387 |
| 315 | A4-M-B51 | 1A | 2.69 | 439 |
| 316 | A4-M-B54 | 1A | 2.7 | 439 |
| 317 | A4-M-B59 | 1A | 3.06 | 453 |
| 318 | A4-M-B60 | 1A | 2.34 | 439 |
| 319 | A4-M-B61 | 1A | 2.33 | 439 |
| 320 | A19-M-B17 | 1A | 3.15 | 419 |
| 321 | A19-M-B64 | 1A | 1.91 | 392 |
| 322 | A19-M-B25 | 1A | 2.95 | 397 |
| 323 | A19-M-B26 | 1A | 2.7 | 385 |
| 324 | A19-M-B28 | 1A | 3.01 | 419 |
| 325 | A19-M-B29 | 1A | 2.46 | 416 |
| 326 | A19-M-B30 | 1A | 2.55 | 443 |
| 327 | A19-M-B31 | 1A | 2.42 | 427 |
| 328 | A19-M-B33 | 1A | 2.46 | 371 |
| 329 | A19-M-B65 | 1A | 2.78 | 427 |
| 330 | A19-M-B34 | 1A | 3.01 | 427 |
| 331 | A19-M-B35 | 1A | 3.28 | 411 |
| 332 | A19-M-B66 | 1A | 3.24 | 419 |
| 333 | A19-M-B37 | 1A | 2.42 | 397 |
| 334 | A19-M-B38 | 1A | 2.64 | 411 |
| 335 | A11-M-B45 | 1A | 2.32 | 456 |
| 336 | A19-M-B40 | 1A | 3.01 | 419 |
| 337 | A19-M-B41 | 1A | 2.81 | 443 |
| 338 | A19-M-B42 | 1A | 2.71 | 443 |
| 339 | A19-M-B67 | 1A | 3.05 | 443 |
| 340 | A11-M-B46 | 1A | 2.8 | 439 |
| 341 | A19-M-B45 | 1A | 2.14 | 442 |
| 342 | A19-M-B52 | 1A | 1.76 | 329 |
| 343 | A19-M-B54 | 1A | 2.74 | 409 |
| 344 | A19-M-B59 | 1A | 3.09 | 423 |
| 345 | A19-M-B68 | 1A | 2.17 | 395 |
| 346 | A19-M-B61 | 1A | 2.36 | 409 |
| 347 | A20-M-B14 | 1A | 3.39 | 484 |
| 348 | A20-M-B15 | 1A | 3.4 | 437 |
| 349 | A20-M-B16 | 1A | 3.23 | 423 |
| 350 | A20-M-B17 | 1A | 4 | 487 |
| 351 | A20-M-B18 | 1A | 3.58 | 477 |
| 352 | A20-M-B64 | 1A | 2.87 | 460 |
| 353 | A20-M-B20 | 1A | 3.46 | 465 |
| 354 | A20-M-B22 | 1A | 3.67 | 473 |
| 355 | A20-M-B23 | 1A | 3.83 | 473 |
| 356 | A20-M-B24 | 1A | 3.81 | 473 |
| 357 | A11-M-B47 | 1A | 2.15 | 357 |
| 358 | A20-M-B26 | 1A | 3.73 | 453 |
| 359 | A20-M-B28 | 1A | 3.93 | 487 |
| 360 | A20-M-B29 | 1A | 3.44 | 484 |
| 361 | A20-M-B30 | 1A | 3.51 | 511 |
| 362 | A20-M-B31 | 1A | 3.4 | 495 |
| 363 | A20-M-B33 | 1A | 3.56 | 439 |
| 364 | A20-M-B36 | 1A | 3.7 | 451 |
| 365 | A20-M-B66 | 1A | 4.07 | 487 |
| 366 | A20-M-B37 | 1A | 3.49 | 465 |
| 367 | A20-M-B39 | 1A | 3.93 | 495 |
| 368 | A20-M-B40 | 1A | 3.93 | 487 |
| 369 | A20-M-B42 | 1A | 3.68 | 511 |
| 370 | A20-M-B67 | 1A | 3.92 | 511 |
| 371 | A20-M-B43 | 1A | 3.53 | 439 |
| 372 | A20-M-B44 | 1A | 3.14 | 453 |
| 373 | A20-M-B45 | 1A | 3.17 | 510 |
| 374 | A20-M-B46 | 1A | 3.58 | 494 |
| 375 | A20-M-B47 | 1A | 3.09 | 411 |
| 376 | A20-M-B49 | 1A | 3.28 | 425 |
| 377 | A20-M-B52 | 1A | 2.75 | 397 |
| 378 | A20-M-B54 | 1A | 3.73 | 477 |
| 379 | A20-M-B59 | 1A | 3.95 | 491 |
| 380 | A20-M-B60 | 1A | 3.33 | 477 |
| 381 | A7-M-B17 | 1A | 3.25 | 431 |
| 382 | A7-M-B64 | 1A | 1.99 | 404 |
| 383 | A7-M-B25 | 1A | 3.06 | 409 |
| 384 | A7-M-B26 | 1A | 2.84 | 397 |
| 385 | A7-M-B28 | 1A | 3.13 | 431 |
| 386 | A7-M-B29 | 1A | 2.56 | 428 |
| 387 | A7-M-B30 | 1A | 2.67 | 455 |
| 388 | A7-M-B31 | 1A | 2.52 | 439 |
| 389 | A7-M-B33 | 1A | 2.58 | 383 |
| 390 | A7-M-B65 | 1A | 2.88 | 439 |
| 391 | A7-M-B34 | 1A | 3.13 | 439 |
| 392 | A7-M-B35 | 1A | 3.38 | 423 |
| 393 | A7-M-B66 | 1A | 3.35 | 431 |
| 394 | A7-M-B37 | 1A | 2.55 | 409 |
| 395 | A7-M-B38 | 1A | 2.75 | 423 |
| 396 | A7-M-B39 | 1A | 3.11 | 439 |
| 397 | A7-M-B40 | 1A | 3.13 | 431 |
| 398 | A7-M-B41 | 1A | 2.92 | 455 |
| 399 | A7-M-B42 | 1A | 2.83 | 455 |
| 400 | A7-M-B67 | 1A | 3.15 | 455 |
| 401 | A7-M-B44 | 1A | 2.19 | 397 |
| 402 | A7-M-B45 | 1A | 2.26 | 454 |
| 403 | A7-M-B52 | 1A | 1.85 | 341 |
| 404 | A7-M-B1 | 1A | 2.65 | 403 |
| 405 | A7-M-B54 | 1A | 2.86 | 421 |
| 406 | A7-M-B59 | 1A | 3.2 | 435 |
| 407 | A11-M-B48 | 1A | 2.82 | 385 |
| 408 | A21-M-B14 | 1A | 3.07 | 496 |
| 409 | A21-M-B15 | 1A | 3.07 | 449 |
| 410 | A21-M-B16 | 1A | 2.8 | 435 |
| 411 | A21-M-B17 | 1A | 3.7 | 499 |
| 412 | A21-M-B18 | 1A | 3.22 | 489 |
| 413 | A21-M-B64 | 1A | 2.51 | 472 |
| 414 | A21-M-B20 | 1A | 3.07 | 477 |
| 415 | A21-M-B22 | 1A | 3.32 | 485 |
| 416 | A21-M-B23 | 1A | 3.5 | 485 |
| 417 | A21-M-B24 | 1A | 3.47 | 485 |
| 418 | A21-M-B25 | 1A | 3.58 | 477 |
| 419 | A21-M-B26 | 1A | 3.39 | 465 |
| 420 | A21-M-B27 | 1A | 3.22 | 451 |
| 421 | A21-M-B28 | 1A | 3.61 | 499 |
| 422 | A21-M-B29 | 1A | 3.05 | 496 |

TABLE III-continued

| Entry | Compound | HPLC Method | HPLC tR (min) | [M + H]+ |
|---|---|---|---|---|
| 423 | A21-M-B30 | 1A | 3.16 | 523 |
| 424 | A21-M-B31 | 1A | 3.02 | 507 |
| 425 | A21-M-B33 | 1A | 3.17 | 451 |
| 426 | A21-M-B34 | 1A | 3.62 | 507 |
| 427 | A21-M-B35 | 1A | 3.8 | 491 |
| 428 | A21-M-B36 | 1A | 3.34 | 463 |
| 429 | A21-M-B66 | 1A | 3.76 | 499 |
| 430 | A21-M-B37 | 1A | 3.1 | 477 |
| 431 | A21-M-B38 | 1A | 3.28 | 491 |
| 432 | A21-M-B39 | 1A | 3.59 | 507 |
| 433 | A21-M-B40 | 1A | 3.61 | 499 |
| 434 | A21-M-B41 | 1A | 3.43 | 523 |
| 435 | A21-M-B42 | 1A | 3.33 | 523 |
| 436 | A21-M-B67 | 1A | 3.61 | 523 |
| 437 | A21-M-B43 | 1A | 3.21 | 451 |
| 438 | A21-M-B44 | 1A | 2.76 | 465 |
| 439 | A21-M-B45 | 1A | 2.73 | 522 |
| 440 | A21-M-B46 | 1A | 3.23 | 505 |
| 441 | A21-M-B47 | 1A | 2.64 | 423 |
| 442 | A21-M-B48 | 1A | 3.27 | 451 |
| 443 | A21-M-B49 | 1A | 2.93 | 437 |
| 444 | A21-M-B50 | 1A | 2.92 | 437 |
| 445 | A21-M-B52 | 1A | 2.37 | 409 |
| 446 | A21-M-B54 | 1A | 3.37 | 489 |
| 447 | A21-M-B59 | 1A | 3.64 | 503 |
| 448 | A21-M-B68 | 1A | 2.75 | 475 |
| 449 | A21-M-B60 | 1A | 2.96 | 489 |
| 450 | A21-M-B61 | 1A | 2.93 | 489 |
| 451 | A22-M-B14 | 1A | 2.48 | 428 |
| 452 | A22-M-B15 | 1A | 2.37 | 381 |
| 453 | A22-M-B16 | 1A | 2.13 | 367 |
| 454 | A22-M-B17 | 1A | 3.15 | 431 |
| 455 | A22-M-B18 | 1A | 2.62 | 421 |
| 456 | A11-M-B49 | 1A | 2.44 | 371 |
| 457 | A22-M-B20 | 1A | 2.43 | 409 |
| 458 | A22-M-B22 | 1A | 2.67 | 417 |
| 459 | A22-M-B23 | 1A | 2.91 | 417 |
| 460 | A22-M-B24 | 1A | 2.88 | 417 |
| 461 | A22-M-B25 | 1A | 2.96 | 409 |
| 462 | A22-M-B26 | 1A | 2.71 | 397 |
| 463 | A22-M-B27 | 1A | 2.54 | 383 |
| 464 | A22-M-B28 | 1A | 3.02 | 431 |
| 465 | A22-M-B29 | 1A | 2.47 | 428 |
| 466 | A22-M-B30 | 1A | 2.56 | 455 |
| 467 | A22-M-B31 | 1A | 2.43 | 439 |
| 468 | A22-M-B33 | 1A | 2.46 | 383 |
| 469 | A22-M-B34 | 1A | 3.03 | 439 |
| 470 | A22-M-B35 | 1A | 3.29 | 423 |
| 471 | A22-M-B36 | 1A | 2.66 | 395 |
| 472 | A22-M-B66 | 1A | 3.25 | 431 |
| 473 | A22-M-B37 | 1A | 2.44 | 409 |
| 474 | A22-M-B38 | 1A | 2.64 | 423 |
| 475 | A22-M-B39 | 1A | 3 | 439 |
| 476 | A22-M-B40 | 1A | 3.02 | 431 |
| 477 | A22-M-B41 | 1A | 2.82 | 455 |
| 478 | A22-M-B42 | 1A | 2.72 | 455 |
| 479 | A22-M-B67 | 1A | 3.07 | 455 |
| 480 | A22-M-B43 | 1A | 2.46 | 383 |
| 481 | A22-M-B44 | 1A | 2.11 | 397 |
| 482 | A22-M-B45 | 1A | 2.16 | 454 |
| 483 | A22-M-B46 | 1A | 2.62 | 437 |
| 484 | A22-M-B47 | 1A | 1.98 | 355 |
| 485 | A22-M-B48 | 1A | 2.61 | 383 |
| 486 | A22-M-B49 | 1A | 2.25 | 369 |
| 487 | A22-M-B51 | 1A | 2.74 | 421 |
| 488 | A22-M-B52 | 1A | 1.76 | 341 |
| 489 | A22-M-B54 | 1A | 2.75 | 421 |
| 490 | A22-M-B59 | 1A | 3.1 | 435 |
| 491 | A23-M-B14 | 1A | 3.04 | 496 |
| 492 | A23-M-B15 | 1A | 3.02 | 449 |
| 493 | A23-M-B16 | 1A | 2.76 | 435 |
| 494 | A23-M-B17 | 1A | 3.65 | 499 |
| 495 | A23-M-B18 | 1A | 3.2 | 489 |
| 496 | A23-M-B64 | 1A | 2.5 | 472 |
| 497 | A23-M-B20 | 1A | 3.04 | 477 |
| 498 | A23-M-B22 | 1A | 3.28 | 485 |
| 499 | A23-M-B23 | 1A | 3.46 | 485 |
| 500 | A23-M-B24 | 1A | 3.42 | 485 |
| 501 | A23-M-B25 | 1A | 3.53 | 477 |
| 502 | A23-M-B26 | 1A | 3.33 | 465 |
| 503 | A23-M-B27 | 1A | 3.16 | 451 |
| 504 | A23-M-B28 | 1A | 3.56 | 499 |
| 505 | A23-M-B29 | 1A | 3.04 | 496 |
| 506 | A23-M-B30 | 1A | 3.13 | 523 |
| 507 | A23-M-B31 | 1A | 2.99 | 507 |
| 508 | A23-M-B33 | 1A | 3.12 | 451 |
| 509 | A23-M-B34 | 1A | 3.59 | 507 |
| 510 | A23-M-B35 | 1A | 3.77 | 491 |
| 511 | A23-M-B36 | 1A | 3.29 | 463 |
| 512 | A23-M-B66 | 1A | 3.73 | 499 |
| 513 | A23-M-B37 | 1A | 3.06 | 477 |
| 514 | A23-M-B38 | 1A | 3.24 | 491 |
| 515 | A23-M-B39 | 1A | 3.56 | 507 |
| 516 | A23-M-B40 | 1A | 3.57 | 499 |
| 517 | A23-M-B41 | 1A | 3.39 | 523 |
| 518 | A23-M-B42 | 1A | 3.31 | 523 |
| 519 | A23-M-B67 | 1A | 3.58 | 523 |
| 520 | A23-M-B43 | 1A | 3.14 | 451 |
| 521 | A23-M-B44 | 1A | 2.7 | 465 |
| 522 | A23-M-B45 | 1A | 2.73 | 522 |
| 523 | A23-M-B46 | 1A | 3.2 | 505 |
| 524 | A23-M-B47 | 1A | 2.6 | 423 |
| 525 | A23-M-B48 | 1A | 3.23 | 451 |
| 526 | A23-M-B49 | 1A | 2.88 | 437 |
| 527 | A23-M-B50 | 1A | 2.85 | 437 |
| 528 | A23-M-B51 | 1A | 3.33 | 489 |
| 529 | A23-M-B52 | 1A | 2.35 | 409 |
| 530 | A23-M-B54 | 1A | 3.34 | 489 |
| 531 | A23-M-B59 | 1A | 3.62 | 503 |
| 532 | A11-M-B54 | 1A | 2.95 | 423 |
| 533 | A23-M-B61 | 1A | 2.9 | 489 |
| 534 | A24-M-B14 | 1A | 3.19 | 492 |
| 535 | A24-M-B15 | 1A | 3.18 | 445 |
| 536 | A24-M-B16 | 1A | 2.92 | 431 |
| 537 | A24-M-B17 | 1A | 3.8 | 495 |
| 538 | A24-M-B18 | 1A | 3.33 | 485 |
| 539 | A24-M-B64 | 1A | 2.66 | 468 |
| 540 | A24-M-B20 | 1A | 3.2 | 473 |
| 541 | A24-M-B22 | 1A | 3.42 | 481 |
| 542 | A24-M-B23 | 1A | 3.59 | 481 |
| 543 | A24-M-B24 | 1A | 3.58 | 481 |
| 544 | A24-M-B25 | 1A | 3.67 | 473 |
| 545 | A24-M-B26 | 1A | 3.49 | 461 |
| 546 | A24-M-B27 | 1A | 3.32 | 447 |
| 547 | A24-M-B28 | 1A | 3.71 | 495 |
| 548 | A24-M-B29 | 1A | 3.19 | 492 |
| 549 | A24-M-B30 | 1A | 3.27 | 519 |
| 550 | A24-M-B31 | 1A | 3.14 | 503 |
| 551 | A24-M-B33 | 1A | 3.27 | 447 |
| 552 | A24-M-B34 | 1A | 3.74 | 503 |
| 553 | A24-M-B35 | 1A | 3.88 | 487 |
| 554 | A24-M-B36 | 1A | 3.44 | 459 |
| 555 | A24-M-B66 | 1A | 3.87 | 495 |
| 556 | A24-M-B37 | 1A | 3.23 | 473 |
| 557 | A24-M-B38 | 1A | 3.38 | 487 |
| 558 | A24-M-B39 | 1A | 3.7 | 503 |
| 559 | A24-M-B40 | 1A | 3.7 | 495 |
| 560 | A24-M-B41 | 1A | 3.54 | 519 |
| 561 | A24-M-B42 | 1A | 3.45 | 519 |
| 562 | A24-M-B67 | 1A | 3.71 | 519 |
| 563 | A24-M-B43 | 1A | 3.31 | 447 |
| 564 | A24-M-B44 | 1A | 2.87 | 461 |
| 565 | A24-M-B45 | 1A | 2.89 | 518 |
| 566 | A24-M-B46 | 1A | 3.34 | 501 |
| 567 | A24-M-B47 | 1A | 2.76 | 419 |
| 568 | A24-M-B48 | 1A | 3.38 | 447 |
| 569 | A24-M-B49 | 1A | 3.06 | 433 |
| 570 | A24-M-B50 | 1A | 3.03 | 433 |
| 571 | A24-M-B52 | 1A | 2.52 | 405 |
| 572 | A24-M-B54 | 1A | 3.49 | 485 |
| 573 | A24-M-B59 | 1A | 3.76 | 499 |
| 574 | A24-M-B60 | 1A | 3.09 | 485 |
| 575 | A25-M-B14 | 1A | 3.23 | 492 |
| 576 | A25-M-B15 | 1A | 3.23 | 445 |

TABLE III-continued

| Entry | Compound | HPLC Method | HPLC tR (min) | [M + H]+ |
|---|---|---|---|---|
| 577 | A25-M-B16 | 1A | 2.97 | 431 |
| 578 | A25-M-B17 | 1A | 3.81 | 495 |
| 579 | A25-M-B18 | 1A | 3.37 | 485 |
| 580 | A25-M-B64 | 1A | 2.71 | 468 |
| 581 | A25-M-B20 | 1A | 3.24 | 473 |
| 582 | A25-M-B22 | 1A | 3.47 | 481 |
| 583 | A25-M-B23 | 1A | 3.63 | 481 |
| 584 | A25-M-B24 | 1A | 3.62 | 481 |
| 585 | A25-M-B25 | 1A | 3.7 | 473 |
| 586 | A25-M-B26 | 1A | 3.53 | 461 |
| 587 | A25-M-B27 | 1A | 3.36 | 447 |
| 588 | A25-M-B28 | 1A | 3.73 | 495 |
| 589 | A25-M-B29 | 1A | 3.23 | 492 |
| 590 | A25-M-B30 | 1A | 3.33 | 519 |
| 591 | A25-M-B31 | 1A | 3.2 | 503 |
| 592 | A25-M-B33 | 1A | 3.33 | 447 |
| 593 | A25-M-B34 | 1A | 3.77 | 503 |
| 594 | A25-M-B35 | 1A | 3.92 | 487 |
| 595 | A25-M-B36 | 1A | 3.48 | 459 |
| 596 | A25-M-B66 | 1A | 3.89 | 495 |
| 597 | A25-M-B37 | 1A | 3.27 | 473 |
| 598 | A25-M-B38 | 1A | 3.41 | 487 |
| 599 | A25-M-B39 | 1A | 3.74 | 503 |
| 600 | A25-M-B40 | 1A | 3.73 | 495 |
| 601 | A25-M-B42 | 1A | 3.49 | 519 |
| 602 | A25-M-B67 | 1A | 3.75 | 519 |
| 603 | A25-M-B43 | 1A | 3.36 | 447 |
| 604 | A25-M-B44 | 1A | 2.92 | 461 |
| 605 | A25-M-B45 | 1A | 2.93 | 518 |
| 606 | A25-M-B46 | 1A | 3.38 | 501 |
| 607 | A25-M-B47 | 1A | 2.83 | 419 |
| 608 | A25-M-B48 | 1A | 3.43 | 447 |
| 609 | A25-M-B49 | 1A | 3.11 | 433 |
| 610 | A25-M-B50 | 1A | 3.09 | 433 |
| 611 | A25-M-B52 | 1A | 2.58 | 405 |
| 612 | A25-M-B54 | 1A | 3.52 | 485 |
| 613 | A25-M-B59 | 1A | 3.78 | 499 |
| 614 | A25-M-B68 | 1A | 2.92 | 471 |
| 615 | A25-M-B61 | 1A | 3.08 | 485 |
| 616 | A26-M-B14 | 1A | 3.39 | 484 |
| 617 | A26-M-B15 | 1A | 3.43 | 437 |
| 618 | A26-M-B16 | 1A | 3.17 | 423 |
| 619 | A26-M-B17 | 1A | 3.97 | 487 |
| 620 | A26-M-B18 | 1A | 3.53 | 477 |
| 621 | A26-M-B64 | 1A | 2.89 | 460 |
| 622 | A26-M-B20 | 1A | 3.42 | 465 |
| 623 | A26-M-B22 | 1A | 3.64 | 473 |
| 624 | A26-M-B23 | 1A | 3.79 | 473 |
| 625 | A26-M-B24 | 1A | 3.78 | 473 |
| 626 | A26-M-B25 | 1A | 3.88 | 465 |
| 627 | A26-M-B27 | 1A | 3.54 | 439 |
| 628 | A26-M-B28 | 1A | 3.88 | 487 |
| 629 | A26-M-B29 | 1A | 3.38 | 484 |
| 630 | A26-M-B30 | 1A | 3.47 | 511 |
| 631 | A26-M-B31 | 1A | 3.35 | 495 |
| 632 | A26-M-B33 | 1A | 3.51 | 439 |
| 633 | A26-M-B34 | 1A | 3.93 | 495 |
| 634 | A26-M-B35 | 1A | 4.07 | 479 |
| 635 | A26-M-B36 | 1A | 3.66 | 451 |
| 636 | A26-M-B66 | 1A | 4.04 | 487 |
| 637 | A26-M-B37 | 1A | 3.45 | 465 |
| 638 | A26-M-B38 | 1A | 3.58 | 479 |
| 639 | A26-M-B39 | 1A | 3.9 | 495 |
| 640 | A26-M-B40 | 1A | 3.89 | 487 |
| 641 | A26-M-B41 | 1A | 3.74 | 511 |
| 642 | A26-M-B42 | 1A | 3.65 | 511 |
| 643 | A26-M-B67 | 1A | 3.89 | 511 |
| 644 | A26-M-B43 | 1A | 3.56 | 439 |
| 645 | A26-M-B45 | 1A | 3.11 | 510 |
| 646 | A26-M-B46 | 1A | 3.54 | 494 |
| 647 | A26-M-B47 | 1A | 3.03 | 411 |
| 648 | A26-M-B48 | 1A | 3.6 | 439 |
| 649 | A26-M-B49 | 1A | 3.3 | 425 |
| 650 | A26-M-B50 | 1A | 3.27 | 425 |
| 651 | A26-M-B52 | 1A | 2.78 | 397 |
| 652 | A26-M-B54 | 1A | 3.7 | 477 |
| 653 | A26-M-B59 | 1A | 3.95 | 491 |
| 654 | A26-M-B61 | 1A | 3.25 | 477 |
| 655 | A27-M-B14 | 1A | 3.14 | 470 |
| 656 | A27-M-B15 | 1A | 3.12 | 423 |
| 657 | A27-M-B16 | 1A | 2.86 | 409 |
| 658 | A27-M-B17 | 1A | 3.77 | 473 |
| 659 | A27-M-B18 | 1A | 3.29 | 463 |
| 660 | A27-M-B64 | 1A | 2.58 | 446 |
| 661 | A27-M-B20 | 1A | 3.15 | 451 |
| 662 | A27-M-B22 | 1A | 3.38 | 459 |
| 663 | A27-M-B23 | 1A | 3.56 | 459 |
| 664 | A27-M-B24 | 1A | 3.55 | 459 |
| 665 | A27-M-B25 | 1A | 3.63 | 451 |
| 666 | A27-M-B26 | 1A | 3.45 | 439 |
| 667 | A27-M-B27 | 1A | 3.27 | 425 |
| 668 | A27-M-B28 | 1A | 3.67 | 473 |
| 669 | A27-M-B29 | 1A | 3.14 | 470 |
| 670 | A27-M-B30 | 1A | 3.23 | 497 |
| 671 | A27-M-B31 | 1A | 3.1 | 481 |
| 672 | A27-M-B33 | 1A | 3.22 | 425 |
| 673 | A27-M-B34 | 1A | 3.7 | 481 |
| 674 | A27-M-B35 | 1A | 3.87 | 465 |
| 675 | A27-M-B36 | 1A | 3.39 | 437 |
| 676 | A27-M-B66 | 1A | 3.83 | 473 |
| 677 | A27-M-B37 | 1A | 3.16 | 451 |
| 678 | A27-M-B38 | 1A | 3.33 | 465 |
| 679 | A27-M-B39 | 1A | 3.67 | 481 |
| 680 | A27-M-B40 | 1A | 3.67 | 473 |
| 681 | A27-M-B41 | 1A | 3.5 | 497 |
| 682 | A27-M-B42 | 1A | 3.4 | 497 |
| 683 | A27-M-B67 | 1A | 3.69 | 497 |
| 684 | A27-M-B43 | 1A | 3.26 | 425 |
| 685 | A27-M-B44 | 1A | 2.8 | 439 |
| 686 | A27-M-B45 | 1A | 2.82 | 496 |
| 687 | A27-M-B46 | 1A | 3.29 | 479 |
| 688 | A27-M-B47 | 1A | 2.7 | 397 |
| 689 | A27-M-B48 | 1A | 3.33 | 425 |
| 690 | A27-M-B49 | 1A | 2.99 | 411 |
| 691 | A27-M-B50 | 1A | 2.97 | 411 |
| 692 | A27-M-B51 | 1A | 3.45 | 463 |
| 693 | A27-M-B54 | 1A | 3.45 | 463 |
| 694 | A27-M-B59 | 1A | 3.73 | 477 |
| 695 | A27-M-B60 | 1A | 3.03 | 463 |
| 696 | A11-M-B59 | 1A | 3.28 | 437 |
| 697 | A1-M-B15 | 1A | 2.86 | 397 |
| 698 | A1-M-B16 | 1A | 2.59 | 383 |
| 699 | A1-M-B17 | 1A | 3.55 | 447 |
| 700 | A1-M-B18 | 1A | 3.05 | 437 |
| 701 | A1-M-B20 | 1A | 2.89 | 425 |
| 702 | A1-M-B22 | 1A | 3.14 | 433 |
| 703 | A1-M-B23 | 1A | 3.33 | 433 |
| 704 | A1-M-B24 | 1A | 3.32 | 433 |
| 705 | A1-M-B25 | 1A | 3.41 | 425 |
| 706 | A1-M-B26 | 1A | 3.21 | 413 |
| 707 | A1-M-B27 | 1A | 3.02 | 399 |
| 708 | A1-M-B28 | 1A | 3.45 | 447 |
| 709 | A1-M-B29 | 1A | 2.89 | 444 |
| 710 | A1-M-B30 | 1A | 2.99 | 471 |
| 711 | A1-M-B33 | 1A | 2.97 | 399 |
| 712 | A1-M-B65 | 1A | 3.23 | 455 |
| 713 | A1-M-B34 | 1A | 3.48 | 455 |
| 714 | A11-M-B60 | 1A | 2.56 | 423 |
| 715 | A1-M-B36 | 1A | 3.14 | 411 |
| 716 | A1-M-B66 | 1A | 3.63 | 447 |
| 717 | A1-M-B37 | 1A | 2.91 | 425 |
| 718 | A1-M-B38 | 1A | 3.09 | 439 |
| 719 | A1-M-B39 | 1A | 3.45 | 455 |
| 720 | A11-M-B61 | 1A | 2.53 | 423 |
| 721 | A1-M-B41 | 1A | 3.26 | 471 |
| 722 | A1-M-B42 | 1A | 3.17 | 471 |
| 723 | A1-M-B43 | 1A | 3 | 399 |
| 724 | A1-M-B45 | 1A | 2.57 | 470 |
| 725 | A1-M-B46 | 1A | 3.06 | 453 |
| 726 | A1-M-B47 | 1A | 2.42 | 371 |
| 727 | A1-M-B48 | 1A | 3.08 | 399 |
| 728 | A1-M-B49 | 1A | 2.72 | 385 |
| 729 | A1-M-B51 | 1A | 3.2 | 437 |
| 730 | A1-M-B52 | 1A | 2.16 | 357 |

49

TABLE III-continued

| Entry | Compound | HPLC Method | HPLC tR (min) | [M + H]+ |
|---|---|---|---|---|
| 731 | A1-M-B54 | 1A | 3.21 | 437 |
| 732 | A1-M-B59 | 1A | 3.52 | 451 |
| 733 | A1-M-B60 | 1A | 2.79 | 437 |
| 734 | A28-M-B17 | 1A | 3.03 | 405 |
| 735 | A28-M-B25 | 1A | 2.82 | 383 |
| 736 | A28-M-B26 | 1A | 2.56 | 371 |
| 737 | A28-M-B28 | 1A | 2.89 | 405 |
| 738 | A28-M-B29 | 1A | 2.34 | 402 |
| 739 | A28-M-B30 | 1A | 2.44 | 429 |
| 740 | A28-M-B31 | 1A | 2.3 | 413 |
| 741 | A28-M-B33 | 1A | 2.33 | 357 |
| 742 | A28-M-B65 | 1A | 2.64 | 413 |
| 743 | A28-M-B34 | 1A | 2.86 | 413 |
| 744 | A28-M-B35 | 1A | 3.15 | 397 |
| 745 | A28-M-B66 | 1A | 3.12 | 405 |
| 746 | A28-M-B37 | 1A | 2.3 | 383 |
| 747 | A28-M-B39 | 1A | 2.85 | 413 |
| 748 | A28-M-B40 | 1A | 2.89 | 405 |
| 749 | A28-M-B41 | 1A | 2.68 | 429 |
| 750 | A28-M-B42 | 1A | 2.57 | 429 |
| 751 | A28-M-B67 | 1A | 2.91 | 429 |
| 752 | A28-M-B45 | 1A | 2.04 | 428 |
| 753 | A28-M-B52 | 1A | 1.67 | 315 |
| 754 | A28-M-B1 | 1A | 2.41 | 377 |
| 755 | A28-M-B54 | 1A | 2.6 | 395 |
| 756 | A28-M-B59 | 1A | 2.97 | 409 |
| 757 | A11-M-B14 | 1A | 2.65 | 430 |
| 758 | A11-M-B15 | 1A | 2.58 | 383 |
| 759 | A11-M-B17 | 1A | 3.33 | 433 |
| 760 | A11-M-B18 | 1A | 2.8 | 423 |
| 761 | A11-M-B20 | 1A | 2.63 | 411 |
| 762 | A11-M-B22 | 1A | 2.87 | 419 |
| 763 | A11-M-B23 | 1A | 3.08 | 419 |
| 764 | A11-M-B24 | 1A | 3.07 | 419 |
| 765 | A11-M-B25 | 1A | 3.15 | 411 |
| 766 | A11-M-B26 | 1A | 2.92 | 399 |
| 767 | A11-M-B27 | 1A | 2.74 | 385 |
| 768 | A11-M-B28 | 1A | 3.21 | 433 |
| 769 | A11-M-B29 | 1A | 2.65 | 430 |
| 770 | A11-M-B30 | 1A | 2.74 | 457 |
| 771 | A25-M-B41 | 1A | 3.58 | 519 |
| 772 | A14-M-B70 | 2 | 5.28 | 546 |
| 773 | A14-M-B71 | 2 | 4.76 | 467 |

Example 2

Preparation of A2-M-B9

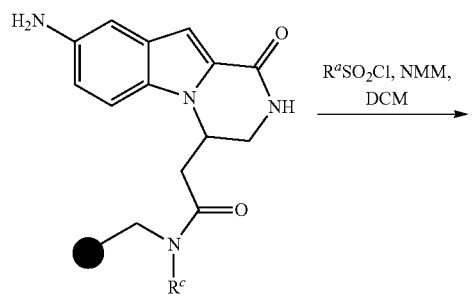

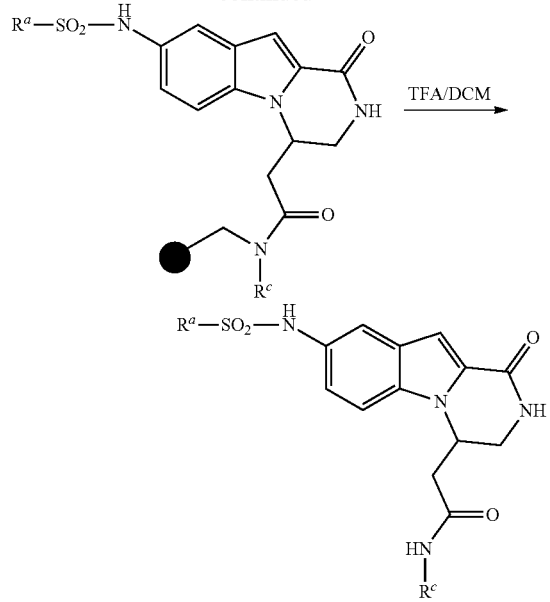

A sulfonyl chloride of formula (X), wherein $R^a$ corresponds to fragment B9 of table II, (0.12 mmol, 1.2 eq.) was added to a suspension of the resin of example 8 wherein Rc corresponds to the fragment A2 of table I (0 1 mmol, 1 eq.) in dry DCM (2.5 ml) and N-methyl morpholine (22.0 μl, 0.2 mmol, 2 eq.). The final suspension was shaken overnight at 25° C. in a reactor (Quest 210™ or Miniblocks™). The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then air dried. The Resin (0.1 mmol, 1 eq.) was suspended in a solution of TFA/DCM 1:1 (2 ml) and shaken for 2 h at 25° C. The solution phase was collected and the resin was rinsed with DCM (collected as well), and a second cycle was performed. The final washing was performed with MeOH. All the collected were dried under reduced pressure affording compound A2-M-B9 (see entry 774 of table IV below).

LCMS (HPLC Method 1B): m/z 519 [M+H]+ @ r.t. 3.2 min $^1$H NMR (400 MHz, DMSO-$d_6$) δ ppm 8.03 (d, J=5.0 Hz, 1H), 7.86 (t, J=5.4 Hz, 1H), 7.66-7.72 (m, 2H), 7.56-7.61 (m, 2H), 7.37 (d, J=8.9 Hz, 1H), 7.33 (d, J=1.8 Hz, 1H), 6.99 (dd, J=9.0, 2.0 Hz, 1H), 6.96 (s, 1H), 4.91-5.00 (m, 1H), 3.77 (dd, J=13.0, 4.5 Hz, 1H), 3.42-3.49 (m, 1H), 2.85-2.94 (m, 2H), 2.38-2.58 (m, 2H), 2.13 (br. s., 8H), 1.29-1.40 (m, 2H).

Following the procedure described in example 10 and by using any proper reactant as per the process of the invention that is, by supporting any suitable amine onto the resin, by sulfonylation the amino function in position 8 of the 3,4-dihydro-2H-pyrazino[1,2-a]indol-1-one moiety with any suitable sulfonyl chloride derivative and by finally carrying out resin cleavage, the following compounds of table IV were also prepared.

TABLE IV

| Entry | Compound | HPLC Method | HPLC tR (min) | [M + H]+ |
|---|---|---|---|---|
| 774 | A2-M-B9 | 1B | 3.2 | 519 |
| 775 | A2-M-B10 | 1B | 2.51 | 490 |
| 776 | A2-M-B11 | 1B | 2.79 | 520 |

TABLE IV-continued

| Entry | Compound | HPLC Method | HPLC tR (min) | [M + H]+ |
|---|---|---|---|---|
| 777 | A3-M-B9 | 1B | 3.25 | 547 |
| 778 | A3-M-B10 | 1B | 2.55 | 518 |
| 779 | A3-M-B11 | 1B | 2.83 | 548 |
| 780 | A4-M-B9 | 1B | 4.46 | 491 |
| 781 | A4-M-B10 | 1B | 3.54 | 463 |
| 782 | A4-M-B11 | 1B | 3.94 | 493 |
| 783 | A5-M-B9 | 1B | 5.45 | 538 |
| 784 | A5-M-B13 | 1B | 4.72 | 509 |
| 785 | A5-M-B10 | 1B | 4.69 | 509 |
| 786 | A5-M-B11 | 1B | 5.04 | 539 |
| 787 | A6-M-B9 | 1B | 5.42 | 504 |
| 788 | A6-M-B10 | 1B | 4.6 | 475 |
| 789 | A6-M-B11 | 1B | 4.97 | 505 |
| 790 | A7-M-B9 | 1B | 4.67 | 473 |
| 791 | A7-M-B10 | 1B | 3.73 | 445 |
| 792 | A7-M-B11 | 1B | 4.14 | 475 |
| 793 | A10-M-B19 | 1A | 1.87 | 421 |
| 794 | A10-M-B21 | 1A | 2.74 | 497 |
| 795 | A10-M-B32 | 1A | 2.02 | 435 |
| 796 | A11-M-B32 | 1A | 2.03 | 393 |
| 797 | A10-M-B55 | 1A | 2.65 | 518 |
| 798 | A10-M-B62 | 1A | 2.95 | 515 |
| 799 | A10-M-B63 | 1A | 2.95 | 519 |
| 800 | A13-M-B19 | 1A | 1.84 | 379 |
| 801 | A13-M-B21 | 1A | 2.78 | 455 |
| 802 | A13-M-B32 | 1A | 1.99 | 393 |
| 803 | A13-M-B55 | 1A | 2.68 | 475 |
| 804 | A13-M-B62 | 1A | 3 | 473 |
| 805 | A13-M-B63 | 1A | 3.01 | 477 |
| 806 | A14-M-B19 | 1A | 2.26 | 427 |
| 807 | A14-M-B21 | 1A | 3.12 | 503 |
| 808 | A14-M-B32 | 1A | 2.42 | 441 |
| 809 | A14-M-B55 | 1A | 3.06 | 524 |
| 810 | A14-M-B62 | 1A | 3.32 | 521 |
| 811 | A14-M-B63 | 1A | 3.33 | 525 |
| 812 | A15-M-B19 | 1A | 2.04 | 393 |
| 813 | A15-M-B21 | 1A | 2.97 | 469 |
| 814 | A15-M-B32 | 1A | 2.21 | 407 |
| 815 | A15-M-B55 | 1A | 2.87 | 489 |
| 816 | A15-M-B62 | 1A | 3.19 | 487 |
| 817 | A15-M-B63 | 1A | 3.21 | 491 |
| 818 | A16-M-B19 | 1A | 2.11 | 405 |
| 819 | A16-M-B21 | 1A | 3.04 | 481 |
| 820 | A16-M-B32 | 1A | 2.29 | 419 |
| 821 | A16-M-B69 | 1A | 2.96 | 481 |
| 822 | A16-M-B55 | 1A | 2.94 | 502 |
| 823 | A16-M-B62 | 1A | 3.25 | 499 |
| 824 | A16-M-B63 | 1A | 3.28 | 503 |
| 825 | A17-M-B19 | 1A | 1.99 | 417 |
| 826 | A17-M-B21 | 1A | 2.88 | 493 |
| 827 | A17-M-B32 | 1A | 2.15 | 431 |
| 828 | A17-M-B62 | 1A | 3.09 | 511 |
| 829 | A17-M-B63 | 1A | 3.09 | 515 |
| 830 | A18-M-B21 | 1A | 3.26 | 517 |
| 831 | A18-M-B32 | 1A | 2.62 | 455 |
| 832 | A18-M-B55 | 1A | 3.18 | 538 |
| 833 | A18-M-B62 | 1A | 3.45 | 535 |
| 834 | A18-M-B63 | 1A | 3.48 | 539 |
| 835 | A4-M-B19 | 1A | 1.73 | 395 |
| 836 | A4-M-B21 | 1A | 2.6 | 471 |
| 837 | A4-M-B32 | 1A | 1.88 | 409 |
| 838 | A4-M-B69 | 1A | 2.49 | 471 |
| 839 | A4-M-B55 | 1A | 2.51 | 491 |
| 840 | A4-M-B62 | 1A | 2.82 | 489 |
| 841 | A4-M-B63 | 1A | 2.8 | 493 |
| 842 | A19-M-B19 | 1A | 1.72 | 365 |
| 843 | A19-M-B21 | 1A | 2.63 | 441 |
| 844 | A19-M-B32 | 1A | 1.87 | 379 |
| 845 | A20-M-B19 | 1A | 2.68 | 433 |
| 846 | A20-M-B21 | 1A | 3.45 | 509 |
| 847 | A20-M-B32 | 1A | 2.84 | 447 |
| 848 | A20-M-B69 | 1A | 3.48 | 509 |
| 849 | A20-M-B55 | 1A | 3.36 | 530 |
| 850 | A20-M-B62 | 1A | 3.63 | 527 |
| 851 | A20-M-B63 | 1A | 3.74 | 531 |
| 852 | A7-M-B19 | 1A | 1.8 | 377 |
| 853 | A7-M-B21 | 1A | 2.73 | 453 |
| 854 | A7-M-B32 | 1A | 1.96 | 391 |
| 855 | A7-M-B55 | 1A | 2.63 | 473 |
| 856 | A7-M-B62 | 1A | 2.95 | 471 |
| 857 | A7-M-B63 | 1A | 2.95 | 475 |
| 858 | A21-M-B19 | 1A | 2.36 | 445 |
| 859 | A21-M-B21 | 1A | 3.21 | 521 |
| 860 | A21-M-B32 | 1A | 2.54 | 459 |
| 861 | A21-M-B55 | 1A | 3.15 | 542 |
| 862 | A21-M-B62 | 1A | 3.39 | 539 |
| 863 | A21-M-B63 | 1A | 3.4 | 543 |
| 864 | A22-M-B19 | 1A | 1.72 | 377 |
| 865 | A22-M-B21 | 1A | 2.63 | 453 |
| 866 | A22-M-B32 | 1A | 1.87 | 391 |
| 867 | A22-M-B55 | 1A | 2.54 | 473 |
| 868 | A22-M-B62 | 1A | 2.85 | 471 |
| 869 | A22-M-B63 | 1A | 2.83 | 475 |
| 870 | A23-M-B19 | 1A | 2.33 | 445 |
| 871 | A23-M-B21 | 1A | 3.16 | 521 |
| 872 | A23-M-B32 | 1A | 2.5 | 459 |
| 873 | A23-M-B55 | 1A | 3.1 | 542 |
| 874 | A23-M-B62 | 1A | 3.34 | 539 |
| 875 | A23-M-B63 | 1A | 3.38 | 543 |
| 876 | A24-M-B19 | 1A | 2.5 | 441 |
| 877 | A24-M-B21 | 1A | 3.3 | 517 |
| 878 | A24-M-B32 | 1A | 2.66 | 455 |
| 879 | A24-M-B69 | 1A | 3.24 | 517 |
| 880 | A24-M-B55 | 1A | 3.23 | 538 |
| 881 | A11-M-B55 | 1A | 2.71 | 475 |
| 882 | A24-M-B62 | 1A | 3.48 | 535 |
| 883 | A24-M-B63 | 1A | 3.51 | 539 |
| 884 | A25-M-B19 | 1A | 2.57 | 441 |
| 885 | A25-M-B21 | 1A | 3.36 | 517 |
| 886 | A25-M-B32 | 1A | 2.72 | 455 |
| 887 | A25-M-B55 | 1A | 3.28 | 538 |
| 888 | A25-M-B62 | 1A | 3.53 | 535 |
| 889 | A25-M-B63 | 1A | 3.57 | 539 |
| 890 | A26-M-B19 | 1A | 2.75 | 433 |
| 891 | A26-M-B21 | 1A | 3.5 | 509 |
| 892 | A26-M-B32 | 1A | 2.9 | 447 |
| 893 | A26-M-B55 | 1A | 3.46 | 530 |
| 894 | A26-M-B62 | 1A | 3.7 | 527 |
| 895 | A26-M-B63 | 1A | 3.73 | 531 |
| 896 | A27-M-B19 | 1A | 2.38 | 419 |
| 897 | A27-M-B21 | 1A | 3.25 | 495 |
| 898 | A27-M-B32 | 1A | 2.57 | 433 |
| 899 | A27-M-B55 | 1A | 3.18 | 516 |
| 900 | A27-M-B62 | 1A | 3.45 | 513 |
| 901 | A27-M-B63 | 1A | 3.48 | 517 |
| 902 | A1-M-B19 | 1A | 2.13 | 393 |
| 903 | A1-M-B21 | 1A | 3.04 | 469 |
| 904 | A1-M-B32 | 1A | 2.3 | 407 |
| 905 | A11-M-B62 | 1A | 3.02 | 473 |
| 906 | A1-M-B55 | 1A | 2.96 | 489 |
| 907 | A1-M-B62 | 1A | 3.25 | 487 |
| 908 | A1-M-B63 | 1A | 3.28 | 491 |
| 909 | A28-M-B19 | 1A | 1.64 | 351 |
| 910 | A28-M-B21 | 1A | 2.52 | 427 |
| 911 | A28-M-B32 | 1A | 1.79 | 365 |
| 912 | A28-M-B55 | 1A | 2.42 | 447 |
| 913 | A28-M-B63 | 1A | 3.1 | 449 |
| 914 | A11-M-B19 | 1A | 1.87 | 379 |
| 915 | A11-M-B63 | 1A | 3.03 | 477 |
| 916 | A11-M-B21 | 1A | 2.81 | 455 |
| 917 | A14-M-B72 | 2 | 5.33 | 557 |

Example 3

Preparation of A7-M-B6

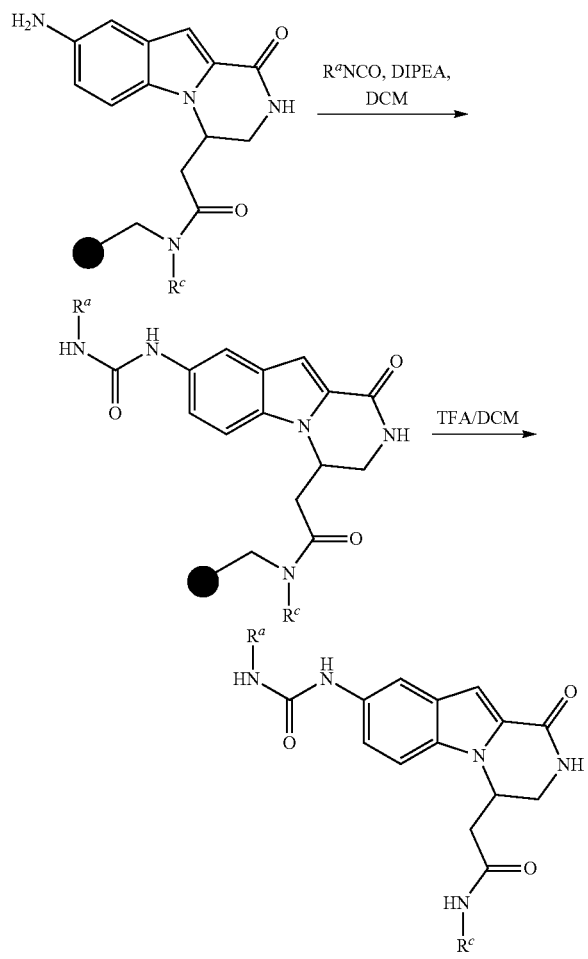

An isocyanate of formula (IX), wherein $R^a$ corresponds to fragment B6 of table II, (0.3 mmol, 3 eq.) was added to a suspension of the resin of example 8 wherein $R^c$ corresponds to the fragment A7 of table I (0.1 mmol, 1 eq.) in dry DCM (2.5 ml) and DIPEA (17.1 μl, 0.1 mmol, 1 eq.). The final suspension was shaken overnight at 25° C. in a reactor (Quest 210™ or Miniblocks™). The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then air dried. The Resin (0.1 mmol, 1 eq.) was suspended in a solution of TFA/DCM 1:1 (2 ml) and shaken for 2 h at 25° C. The solution phase was collected and the resin was rinsed with DCM (collected as well), and a second cycle was performed. The final washing was performed with MeOH. All the collected were dried under reduced pressure affording compound A7-M-B6 (see entry 937 of table V below).

LCMS (HPLC Method 1B): m/z 448 [M+H]$^+$ @ r.t. 4.3 min. $^1$H NMR (400 MHz, DMSO-$d_6$) δ ppm 8.51 (s, 1H), 8.46 (s, 1H), 8.11 (t, J=5.6 Hz, 1H), 8.00 (d, J=5.0 Hz, 1H), 7.83 (d, J=1.7 Hz, 1H), 7.43 (d, J=8.9 Hz, 1H), 7.34-7.39 (m, 2H), 7.24 (dd, J=9.0, 2.0 Hz, 1H), 6.97 (s, 1H), 6.84-6.89 (m, 2H), 5.59-5.71 (m, 1H), 4.95-5.04 (m, 3H), 3.83 (dd, J=12.9, 4.0 Hz, 1H), 3.72 (s, 3H), 3.60-3.65 (m, 2H), 3.49 (dd, J=13.4, 5.2 Hz, 1H), 2.57-2.64 (m, 1H), 2.46-2.53 (m, 1H).

Following the procedure described in example 11 and by using any proper reactant as per the process of the invention, that is by supporting any suitable amine onto the resin, by preparing the carbamate derivative in position 8 of the 3,4-dihydro-2H-pyrazino[1,2-a]indol-1-one moiety with any suitable isocyanate derivative and by finally carrying out resin cleavage, the following compounds of table V were also prepared.

TABLE V

| Entry | Compound | HPLC Method | HPLC tR (min) | [M + H]+ |
|---|---|---|---|---|
| 918 | A2-M-B5 | 1B | 3.16 | 469 |
| 919 | A2-M-B6 | 1B | 2.93 | 493 |
| 920 | A2-M-B7 | 1B | 3.14 | 491 |
| 921 | A3-M-B5 | 1B | 3.23 | 497 |
| 922 | A3-M-B6 | 1B | 2.99 | 521 |
| 923 | A3-M-B7 | 1B | 3.22 | 519 |
| 924 | A4-M-B5 | 1B | 4.6 | 442 |
| 925 | A4-M-B6 | 1B | 4.09 | 466 |
| 926 | A4-M-B7 | 1B | 4.57 | 464 |
| 927 | A4-M-B8 | 1B | 5.46 | 504 |
| 928 | A5-M-B5 | 1B | 5.66 | 488 |
| 929 | A5-M-B6 | 1B | 5.15 | 512 |
| 930 | A5-M-B7 | 1B | 5.61 | 510 |
| 931 | A5-M-B8 | 1B | 6.23 | 550 |
| 932 | A6-M-B5 | 1B | 5.63 | 454 |
| 933 | A6-M-B6 | 1B | 5.12 | 478 |
| 934 | A6-M-B7 | 1B | 5.58 | 476 |
| 935 | A6-M-B8 | 1B | 6.23 | 516 |
| 936 | A7-M-B5 | 1B | 4.84 | 424 |
| 937 | A7-M-B6 | 1B | 4.3 | 448 |
| 938 | A7-M-B7 | 1B | 4.8 | 446 |
| 939 | A7-M-B8 | 1B | 5.65 | 486 |
| 940 | A8-M-B5 | 1B | 3.26 | 469 |
| 941 | A8-M-B7 | 1B | 3.26 | 491 |
| 942 | A9-M-B7 | 1B | 3.36 | 497 |
| 943 | A10-M-B5 | 1A | 3.06 | 468 |
| 944 | A10-M-B53 | 1A | 2.75 | 454 |
| 945 | A10-M-B56 | 1A | 2.68 | 442 |
| 946 | A10-M-B57 | 1A | 1.86 | 400 |
| 947 | A10-M-B58 | 1A | 2.04 | 444 |
| 948 | A13-M-B5 | 1A | 3.13 | 426 |
| 949 | A13-M-B53 | 1A | 2.82 | 412 |
| 950 | A13-M-B56 | 1A | 2.74 | 400 |
| 951 | A13-M-B57 | 1A | 1.85 | 358 |
| 952 | A13-M-B58 | 1A | 2.05 | 402 |
| 953 | A14-M-B5 | 1A | 3.48 | 474 |
| 954 | A14-M-B53 | 1A | 3.21 | 460 |
| 955 | A14-M-B56 | 1A | 3.13 | 448 |
| 956 | A14-M-B57 | 1A | 2.26 | 406 |
| 957 | A15-M-B5 | 1A | 3.36 | 440 |
| 958 | A15-M-B56 | 1A | 2.97 | 414 |
| 959 | A15-M-B57 | 1A | 2.06 | 372 |
| 960 | A16-M-B5 | 1A | 3.43 | 452 |
| 961 | A16-M-B53 | 1A | 3.13 | 438 |
| 962 | A16-M-B56 | 1A | 3.06 | 426 |
| 963 | A16-M-B57 | 1A | 2.14 | 384 |
| 964 | A16-M-B58 | 1A | 2.33 | 428 |
| 965 | A17-M-B5 | 1A | 3.24 | 464 |
| 966 | A17-M-B53 | 1A | 2.94 | 450 |
| 967 | A17-M-B56 | 1A | 2.86 | 438 |
| 968 | A17-M-B57 | 1A | 2 | 396 |
| 969 | A17-M-B58 | 1A | 2.18 | 440 |
| 970 | A18-M-B5 | 1A | 3.61 | 488 |
| 971 | A18-M-B53 | 1A | 3.36 | 474 |
| 972 | A18-M-B56 | 1A | 3.31 | 462 |
| 973 | A18-M-B57 | 1A | 2.46 | 420 |
| 974 | A18-M-B58 | 1A | 2.57 | 464 |
| 975 | A4-M-B53 | 1A | 2.62 | 428 |
| 976 | A4-M-B56 | 1A | 2.52 | 416 |
| 977 | A4-M-B57 | 1A | 1.73 | 374 |
| 978 | A19-M-B5 | 1A | 2.97 | 412 |
| 979 | A19-M-B53 | 1A | 2.63 | 398 |
| 980 | A19-M-B56 | 1A | 2.56 | 386 |

TABLE V-continued

| Entry | Compound | HPLC Method | HPLC tR (min) | [M + H]+ |
|---|---|---|---|---|
| 981 | A19-M-B57 | 1A | 1.73 | 344 |
| 982 | A19-M-B58 | 1A | 1.92 | 388 |
| 983 | A20-M-B5 | 1A | 3.9 | 480 |
| 984 | A20-M-B53 | 1A | 3.68 | 466 |
| 985 | A20-M-B56 | 1A | 3.63 | 454 |
| 986 | A20-M-B58 | 1A | 2.96 | 456 |
| 987 | A7-M-B53 | 1A | 2.76 | 410 |
| 988 | A7-M-B57 | 1A | 1.81 | 356 |
| 989 | A7-M-B58 | 1A | 2.01 | 400 |
| 990 | A21-M-B5 | 1A | 3.58 | 492 |
| 991 | A21-M-B53 | 1A | 3.33 | 478 |
| 992 | A21-M-B56 | 1A | 3.24 | 466 |
| 993 | A21-M-B57 | 1A | 2.36 | 424 |
| 994 | A21-M-B58 | 1A | 2.55 | 468 |
| 995 | A22-M-B5 | 1A | 2.98 | 424 |
| 996 | A22-M-B53 | 1A | 2.65 | 410 |
| 997 | A22-M-B56 | 1A | 2.56 | 398 |
| 998 | A22-M-B57 | 1A | 1.74 | 356 |
| 999 | A11-M-B53 | 1A | 2.85 | 412 |
| 1000 | A23-M-B5 | 1A | 3.52 | 492 |
| 1001 | A23-M-B53 | 1A | 3.27 | 478 |
| 1002 | A23-M-B56 | 1A | 3.2 | 466 |
| 1003 | A23-M-B57 | 1A | 2.32 | 424 |
| 1004 | A23-M-B58 | 1A | 2.51 | 468 |
| 1005 | A24-M-B5 | 1A | 3.66 | 488 |
| 1006 | A24-M-B53 | 1A | 3.42 | 474 |
| 1007 | A24-M-B57 | 1A | 2.5 | 420 |
| 1008 | A24-M-B58 | 1A | 2.67 | 464 |
| 1009 | A25-M-B5 | 1A | 3.71 | 488 |
| 1010 | A25-M-B53 | 1A | 3.46 | 474 |
| 1011 | A25-M-B56 | 1A | 3.4 | 462 |
| 1012 | A25-M-B57 | 1A | 2.56 | 420 |
| 1013 | A25-M-B58 | 1A | 2.72 | 464 |
| 1014 | A26-M-B5 | 1A | 3.89 | 480 |
| 1015 | A11-M-B56 | 1A | 2.77 | 400 |
| 1016 | A11-M-B57 | 1A | 1.89 | 358 |
| 1017 | A26-M-B53 | 1A | 3.65 | 466 |
| 1018 | A26-M-B56 | 1A | 3.6 | 454 |
| 1019 | A26-M-B57 | 1A | 2.76 | 412 |
| 1020 | A26-M-B58 | 1A | 2.92 | 456 |
| 1021 | A27-M-B5 | 1A | 3.64 | 466 |
| 1022 | A27-M-B53 | 1A | 3.38 | 452 |
| 1023 | A27-M-B56 | 1A | 3.31 | 440 |
| 1024 | A27-M-B57 | 1A | 2.41 | 398 |
| 1025 | A27-M-B58 | 1A | 2.59 | 442 |
| 1026 | A11-M-B58 | 1A | 2.09 | 402 |
| 1027 | A1-M-B5 | 1A | 3.43 | 440 |
| 1028 | A1-M-B53 | 1A | 3.13 | 426 |
| 1029 | A1-M-B56 | 1A | 3.05 | 414 |
| 1030 | A1-M-B57 | 1A | 2.14 | 372 |
| 1031 | A1-M-B58 | 1A | 2.34 | 416 |
| 1032 | A28-M-B5 | 1A | 2.84 | 398 |
| 1033 | A28-M-B53 | 1A | 2.51 | 384 |
| 1034 | A28-M-B57 | 1A | 1.64 | 330 |
| 1035 | A28-M-B58 | 1A | 1.83 | 374 |
| 1036 | A11-M-B5 | 1A | 3.16 | 426 |
| 1037 | A14-M-B73 | 2 | 4.53 | 482 |
| 1038 | A14-M-B74 | 2 | 3.83 | 434 |

Example 4

Preparation of A14-M-B76

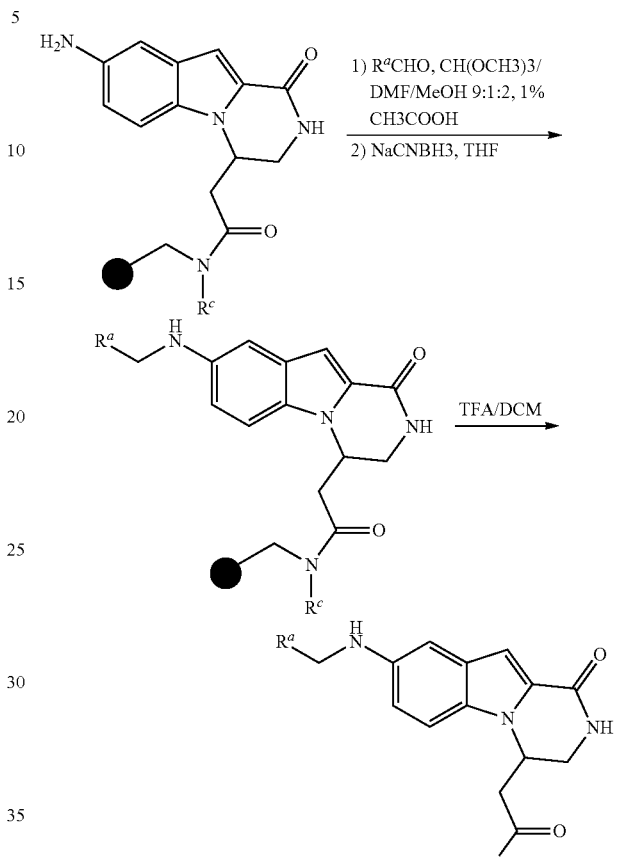

An aldehyde of formula (XIII, wherein $R^a$ corresponds to the fragment B76 of table II, (1.0 mmol, 10 eq.) was added to a suspension of the resin of example 8 wherein $R^c$ corresponds to the fragment A14 of table I (0.1 mmol, 1 eq.) in a dry mixture $CH(OCH_3)_3$/DMF/MeOH 9:1:2 (2 ml) and acetic acid (20 μl). The final suspension was shaken overnight at 25° C. in a reactor (Quest 210™ or Miniblocks™). The resin was washed sequentially with DMF (1 ml), DCM (1 ml), DMF (1 ml), DCM (1 ml). The Resin (0.1 mmol, 1 eq.) was suspended in THF, $NaCNBH_3$ (314 mg, 5.0 mmol, 50 eq.) was added and the final suspension was shaken for 16 h at 25° C. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), MTBE (1 ml, 2 cycles) and then air dried. The Resin (0 1 mmol, 1 eq.) was suspended in a solution of TFA/DCM 1:1 (2 ml) and shaken for 2 h at 25° C. The solution phase was collected and the resin was rinsed with DCM (collected as well), and a second cycle was performed. The final washing was performed with MeOH. All the collected were dried under reduced pressure affording compound A14-M-B76 (see entry 1039 of table VI below).

LCMS (HPLC Method 2): m/z 517 [M+H]$^+$ @ r.t. 5.91 min $^1$H NMR (400 MHz, DMSO-d$_6$) δ ppm 8.40 (t, J=5.7 Hz, 2 H), 7.87-8.04 (m, 2 H), 7.27-7.33 (m, 2 H), 7.01 (dd, J=7.6, 1.6 Hz, 3 H), 4.88-5.08 (m, 2 H), 4.38 (s, 3 H), 4.06-4.26 ppm (m, 4 H).

Following the procedure described in example 12 and by using any proper reactant as per the process of the invention, that is by supporting any suitable amine onto the resin, by preparing the amino derivative in position 8 of the 3,4-dihydro-2H-pyrazino[1,2-a]indol-1-one moiety with any suitable aldehyde derivative and by finally carrying out resin cleavage, the following compounds of table VI were also prepared.

TABLE VI

| Entry | Compound | HPLC Method | HPLC tR (min) | [M + H]+ |
|---|---|---|---|---|
| 1039 | A14-M-B75 | 2 | 6.27 | 445 |
| 1040 | A14-M-B76 | 2 | 5.91 | 517 |

The invention claimed is:

1. A method for treating a disease caused by and/or associated with a dysregulated protein kinase activity which comprises administering to a mammal in need thereof an effective amount of a compound of formula (I)

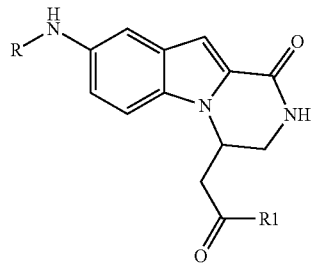

(I)

wherein

R is selected from the group consisting of —$R^a$, —$COR^a$, —$CONR^aR^b$, —$SO_2R^a$ and —$COOR^a$, and R1 is a group —$NR^cR^d$ or —$OR^c$, wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, heterocyclyl or heterocyclyl $C_1$-$C_6$ alkyl, aryl or aryl $C_1$-$C_6$ alkyl, heteroaryl or heteroaryl $C_1$-$C_6$ alkyl or, taken together with the nitrogen atom to which they are bonded, either $R^a$ and $R^b$ as well as $R^c$ and $R^d$ may form an optionally substituted 3 to 7 membered heterocyclyl or heteroaryl, optionally containing one additional heteroatom or heteroatomic group selected from S, O, N or NH, and pharmaceutically acceptable salts thereof, wherein the disease is selected from the group consisting of ovarian cancer and breast cancer.

2. An in vitro method for inhibiting protein kinase activity which comprises contacting the kinase with an effective amount of a compound of formula (I)

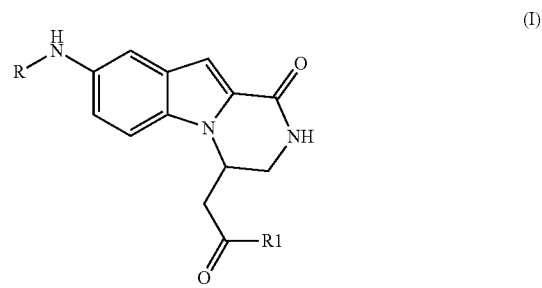

(I)

wherein

R is selected from the group consisting of —$R^a$, —COR, —$CONR^aR^b$, —$SO_2R^a$ and —$COOR^a$, and R1 is a group —$NR^cR^d$ or —$OR^c$, wherein $R^a$, $R^b$, $R^c$ and $R^d$, the same or different, are each independently hydrogen or a group optionally further substituted, selected from straight or branched $C_1$-$C_6$ alkyl, $C_2$-$C_6$, alkenyl or $C_2$-$C_6$ alkynyl, $C_3$-$C_6$ cycloalkyl or cycloalkyl $C_1$-$C_6$ alkyl, heterocyclyl or heterocyclyl $C_1$-$C_6$ alkyl, aryl or aryl $C_1$-$C_6$ alkyl, heteroaryl or heteroaryl $C_1C_6$ alkyl or, taken together with the nitrogen atom to which they are bonded, either $R^a$ and $R^b$ as well as $R^c$ and $R^d$ may form an optionally substituted 3 to 7 membered heterocyclyl or heteroaryl, optionally containing one additional heteroatom or heteroatomic group selected from S, O, N or NH, and pharmaceutically acceptable salts thereof, wherein the kinase is selected from the group consisting of LCK, EGFR1, JAK2, ROS1, FGFR1, ALK, ABL, AUR1, AUR2, CDK2/CYCA, IGFR1, IR, KIT, MET, NEK6, TRKA, and VEGFR3.

* * * * *